(12) United States Patent
Touitou et al.

(10) Patent No.: US 11,389,404 B2
(45) Date of Patent: Jul. 19, 2022

(54) COMPOSITIONS AND METHODS FOR NASAL ADMINISTRATION OF DRUGS TO BRAIN AND FOR SYSTEMIC EFFECT

(71) Applicant: YISSUM RESEARCH DEVELOPMENT COMPANY OF THE HEBREW UNIVERSITY OF JERUSALEM LTD, Jerusalem (IL)

(72) Inventors: Elka Touitou, Hod Hasharon (IL); Hiba Natsheh, Jerusalem (IL)

(73) Assignee: YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 0 days.

(21) Appl. No.: 16/814,163

(22) Filed: Mar. 10, 2020

(65) Prior Publication Data
US 2020/0268662 A1    Aug. 27, 2020

Related U.S. Application Data

(63) Continuation of application No. PCT/IL2018/051004, filed on Sep. 6, 2018.

(60) Provisional application No. 62/556,509, filed on Sep. 11, 2017.

(51) Int. Cl.
| | |
|---|---|
| A61K 9/107 | (2006.01) |
| A61P 25/16 | (2006.01) |
| A61K 38/095 | (2019.01) |
| A61K 9/00 | (2006.01) |
| A61K 31/047 | (2006.01) |
| A61K 31/05 | (2006.01) |
| A61K 31/135 | (2006.01) |
| A61K 31/165 | (2006.01) |
| A61K 31/192 | (2006.01) |
| A61K 31/4196 | (2006.01) |
| A61K 31/426 | (2006.01) |
| A61K 31/485 | (2006.01) |
| A61K 31/551 | (2006.01) |
| A61K 38/12 | (2006.01) |
| A61K 38/18 | (2006.01) |
| A61K 38/28 | (2006.01) |
| A61K 47/02 | (2006.01) |
| A61K 47/10 | (2017.01) |
| A61K 47/24 | (2006.01) |

(52) U.S. Cl.
CPC .......... A61K 9/1075 (2013.01); A61K 9/0043 (2013.01); A61K 31/047 (2013.01); A61K 31/05 (2013.01); A61K 31/135 (2013.01); A61K 31/165 (2013.01); A61K 31/192 (2013.01); A61K 31/4196 (2013.01); A61K 31/426 (2013.01); A61K 31/485 (2013.01); A61K 31/551 (2013.01); A61K 38/095 (2019.01); A61K 38/12 (2013.01); A61K 38/1808 (2013.01); A61K 38/28 (2013.01); A61K 47/02 (2013.01); A61K 47/10 (2013.01); A61K 47/24 (2013.01); A61P 25/16 (2018.01)

(58) Field of Classification Search
CPC ....................................................... A61P 25/16
See application file for complete search history.

(56) References Cited

U.S. PATENT DOCUMENTS

| | | | |
|---|---|---|---|
| 3,968,112 A | 7/1976 | Kornfeld et al. | |
| 4,206,225 A | 6/1980 | Johnson | |
| 4,232,018 A | 11/1980 | Johnson | |
| 4,235,913 A | 11/1980 | Johnson et al. | |
| 4,243,674 A | 1/1981 | Bindra | |
| 4,260,764 A | 4/1981 | Johnson | |
| 4,263,438 A | 4/1981 | Althuis et al. | |
| 4,270,005 A | 5/1981 | Althuis et al. | |
| 4,283,569 A | 8/1981 | Althuis et al. | |
| 4,371,720 A | 2/1983 | Johnson et al. | |
| 4,663,474 A | 5/1987 | Urban | |
| 4,876,276 A | 10/1989 | Mechoulam et al. | |
| 5,112,842 A | 5/1992 | Zierenberg et al. | |
| 5,521,215 A | 5/1996 | Kloog et al. | |
| 6,162,829 A | 12/2000 | Burstein | |
| 7,157,480 B2 | 1/2007 | Bennett | |
| 8,911,751 B2 | 12/2014 | Touitou | |
| 2005/0281772 A1* | 12/2005 | Bromley | A61K 7/06 424/70.14 |

(Continued)

FOREIGN PATENT DOCUMENTS

| | | |
|---|---|---|
| WO | 2001006987 A2 | 2/2001 |
| WO | 2007043057 A2 | 4/2007 |

OTHER PUBLICATIONS

Murat Imer et al, "Effect of magnesium, MK-801 and combination of magnesium and MK-801 on blood-brain barrier permeability and brain edema after experimental traumatic diffuse brain injury", pub date Jul. 19, 2013, Neurological Research, vol. 31, pp. 977-981. (Year: 2013).*

(Continued)

*Primary Examiner* — Mark V Stevens
*Assistant Examiner* — Alparslan Asan
(74) *Attorney, Agent, or Firm* — Browdy and Neimark, PLLC

(57) ABSTRACT

The invention relates to a nasally administrable composition comprising at least one active substance in magnesium-containing vesicular carrier, said carrier comprising glycol, phospholipids, water and at least one magnesium source. Methods for nasal administration of the composition, for example, for pain relief, are also provided.

21 Claims, 10 Drawing Sheets

(56) References Cited

U.S. PATENT DOCUMENTS

Figure 1:
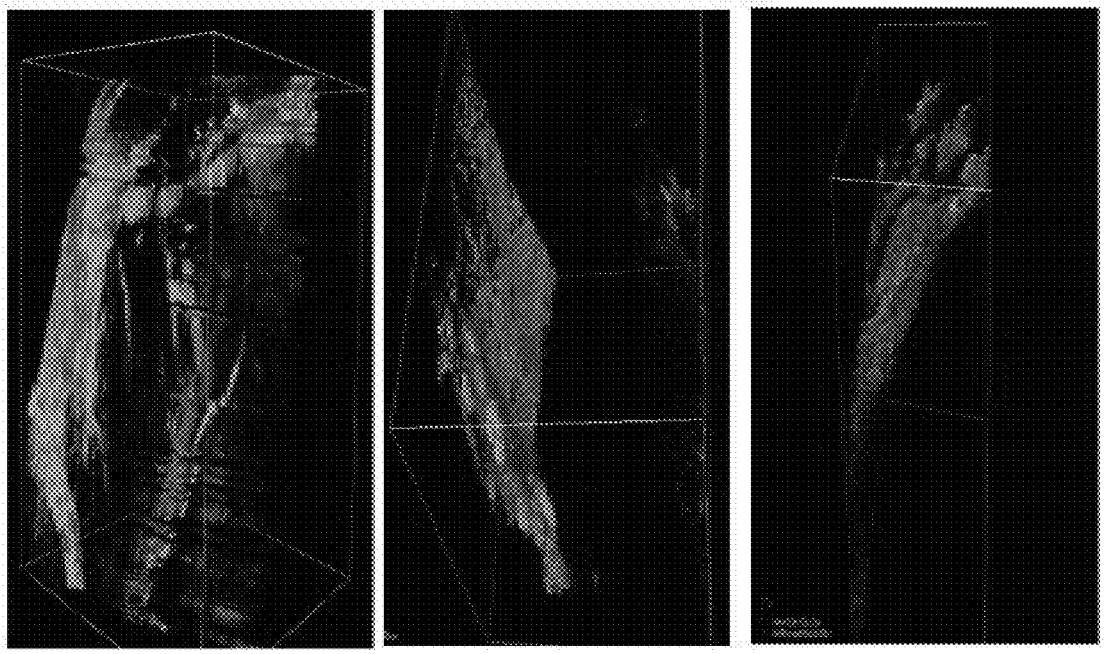

2013/0116215 A1* 5/2013 Coma .................. A61K 45/06
2016/0220604 A1* 8/2016 Buechel ............... A61K 33/06

OTHER PUBLICATIONS

Esen et al., "Effect of magnesium sulfate administration on blood-brain barrier in a rat model of intraperitoneal sepsis: a randomized controlled experimental study", Critical Care, pp. 1-6, vol. 9, No. 1 (Nov. 2004).

Natsheh et al., "Phospholipid Magnesome—a nasal vesicular carrier for delivery of drugs to brain" Germany, pp. 806-819, vol. 8, No. 3 (Mar. 2018).

Baek et al., "Boron Trifluoride Etherate on Alimina—A Modified Lewis Acid Reagent. An Improved Synthesis of Cannabidiol", Tetrahedron Letters, pp. 1083-1086, vol. 26, No. 8, (1985).

Petrzilka et al. "Synthese von Haschisch-Inhaltsstoffen", Helv. Chim. Acta, pp. 1102-1134, vol. 52, No. 4 (1969).

Cope et al., "An Oxygen Insertion Reaction of Osuloses", Department of Chemistry, Massachusetts Institute of Technology, pp. 3273-3275, (Jan. 1965).

Novak et al., "Cannabis XXIV. A New Convenient Synthesis of Cannabinol" Tetrahedron Letters, pp. 253-254, vol. 23, No. 2 (1982).

Teske et al., "A Cyclotrimerization Route to Cannabinoids" Organic Letters, pp. 2195-2198, vol. 10, No. 11 (Mar. 2008).

Siegel et al. An Optically Active Terpenic Synthon for $\Delta 9$-Cannabinoids: Synthesis of (−)-II-Hydroxy-$\Delta 9$-tetrahydrocannabinol (THC) and Its 1', 1'-Dimethylheptyl Analogue, J. Org. Chem., pp. 5428-5430, vol. 54 (1989).

Raj et al. "Pramipexole dihydrochloride loaded chitosan nanoparticles for noseto brain delivery: Development, characterization and in vivoanti-Parkinson activity", International Journal of Biological Macromolecules, pp. 27-35, vol. 109 (2018).

* cited by examiner

COMPOSITIONS AND METHODS FOR NASAL ADMINISTRATION OF DRUGS TO BRAIN AND FOR SYSTEMIC EFFECT

The present invention is directed to pharmaceutical compositions for nasal administration of biologically active agents.

Nasal delivery can provide drug absorption into the systemic circulation and it has been suggested that this route of administration can offer a pathway to transport drugs the brain. There exists a need for an effective carrier to enable enhanced nasal delivery of pharmaceutically active agents.

In WO 01/06987 a carrier is disclosed, in which the major component is an ethanol/propylene glycol mixture. The carrier contains from 10 to 80% by volume of an aliphatic alcohol, 10 to 80% by volume of a glycol and 0.1 to 5% by weight of a bile salt or lecithin for administering anticonvulsive agent. The examples of WO 01/06987 illustrate a vehicle with water content of 10%.

In U.S. Pat. No. 8,911,751, Touitou et al. describe the intranasal administration of active ingredients to the systemic circulation or brain with the aid of a vesicular carrier containing water: alcohol: glycol: phospholipids proportioned>30%: 12-30%: 1-30%: 0.2-10%, respectively, expressed by weight percentage.

Delivery to brain of many molecules is difficult to achieve and presents a challenge. We have surprisingly found that addition of magnesium ion to a carrier containing what we call soft phospholipid vesicles, enhances the delivery to brain and systemic action of the active molecule.

The composition of the invention, i.e., a soft phospholipid vesicle that contains magnesium, displaying enhanced nasal delivery properties to the brain and systemic action, is named herein "phospholipid magnesome" (magnesium-containing vesicular carrier).

The invention provides a nasally administrable composition comprising an active substance (in particular a physiologically/pharmaceutically active substance) in a magnesium-containing vesicular carrier, i.e., a carrier comprising glycol, phospholipids, at least one magnesium source and water. Hence, in its most general form, phospholipid magnesome is based on a vesicular carrier made of glycol: phospholipids: magnesium ion and water.

The invention also provides a method of administering pharmaceutically active ingredient to a mammal in need thereof, for treating various conditions as described below, which method comprises the intranasal administration of a composition comprising a therapeutically effective amount of said active ingredient in a magnesium-containing vesicular carrier, i.e., a carrier comprising glycol, phospholipids, at least one magnesium source and water.

The experimental results reported below indicate that the magnesium-containing vesicular carrier of the invention enhances the delivery of drugs to the brain via the intranasal route. Accordingly, another aspect of the invention is a method of increasing the delivery of a physiologically active compound from a nasally administrable composition to the brain and /or bloodstream of mammals, the method comprises incorporating magnesium source into a vesicular carrier comprising glycol, phospholipids, water and physiologically active compound, e.g., CNS-active drugs.

The concentration ranges of the constituents of phospholipid magnesome as set forth herein are by weight percentage, based on the total weight of the composition (unless indicated otherwise).

The concentration of the glycol in the composition (e.g., propylene glycol) is not less than 5% by weight, e.g., up to 50%, for example, 10-50% by weight (e.g., 10-40%). The water content of phospholipid magnesome is not less than 20% by weight, e.g., not less than 30%, e.g., not less than 50%.

Phospholipids suitable for use in the preparation of the composition according to the present invention include phosphoglycerides, e.g., phosphatidylcholine (lecithin, such as soy and egg lecithin). Other phospholipids are hydrogenated phosphatidylcholine, phosphatidylserine, phosphatidylethanolamine, phosphatidylglycerol and phosphatidylinositol. Preferably, the phospholipids are present in the composition of the invention at a concentration of 0.1 to 15% by weight, e.g., 0.2 to 10% by weight. Suitable products are phosphatidylcholine commercially available from various sources, for example, from Lipoid under the brand names of Phospholipon®: the 85 G, 90G and 80 H, 90H grades; Lipoid®: Lipoid 100S PC, Lipoid S 100, Lipoid S 75, and others.

Suitable magnesium sources are compounds which dissociate in the liquid carrier to release magnesium ion ($Cm^{2+}$), e.g., pharmaceutically acceptable water-soluble magnesium salts such as magnesium sulfate, magnesium chloride, magnesium L-aspartate, magnesium stearate and magnesium alginate, including their hydrated forms. The concentration of the magnesium salt is not less than 0.002%, e.g., from 0.005 to 5.0% by weight, preferably not less than 0.01% by weight, e.g., from 0.01 to 1.0% by weight or from 0.01 to 5% by weight. But the magnesium source could also be added at higher concentrations, e.g., up to 20% by weight.

Mucoadhesive agents can be added to improve adhesion of phospholipid magnesome to the nasal mucous membrane, for example, hydroxypropyl cellulose, carbomer and alginates, e.g., gel-forming agents. The desired concentration of the mucoadhesive agent depends on the properties of the agent selected and the desired mucoadhesivity. In general, the concentration of this additive varies from 0.1 to 10% by weight.

Alcohol, such as ethanol and isopropanol, is not a mandatory component of phospholipid magnesome, but can be part of the composition, e.g., up to 25% by weight, for example, from 1 to 25% by weight. However, as shown below, the compositions are preferably free of aliphatic monohydroxy alcohols (e.g., devoid of C2-C5 alcohols, such as ethanol and isopropanol).

Antioxidants can be added to maintain the stability of the product. Some examples of antioxidants include tocopherols (vitamin E), butyl hydroxytoluene, sodium metabisulfite, potassium metabisulfite, ascorbyl palmitate and the like. These antioxidants may be present in the formulations in a concentration of from about 0.05 to 1.0% w/w.

One method to prepare phospholipid magnesome is by dissolving phospholipids in the glycol component, or in a mixture of glycol and alcohol, adding the physiologically active substance and the other ingredients, including of course the magnesium source, and finally combining the glycolic/alcoholic component and the aqueous component. The magnesium source is generally added in the form of a separately prepared aqueous solution, but of course, it could also be employed in a solid form to be dissolved directly in the carrier.

In some cases, the total amount of water needed for the composition is divided such that a portion, say, up to 20-30% of the total water amount, is added in conjunction with the physiologically active substance or other ingredients. Some physiologically active substances require basification or acidification of the medium to facilitate their dissolution. These physiologically active substances are first separately dissolved in an alkaline aqueous solution (or acidic aqueous solution, as required) followed by respective pH adjustment, and the clear aqueous solution with the physiologically active substance is mixed with the magnesium salt solution and the remaining amount of water and the resultant aqueous phase is combined with the phospholipids solution to form the composition. The preparation of the composition is carried out by mixing under various methods, homogenization or stirring, typically at room temperature or at an elevated temperature. To prepare forms of phospholipid magnesome capable of being adhered to nasal mucous membrane, as mentioned above, a gel component (e.g., alginate, carbomer) is prepared separately, the aqueous solution of the magnesium compound is added to the gel which is ultimately combined with the phospholipids solution under stirring.

The experimental results reported below show that phospholipid magnesome achieves more efficient delivery via the nasal route into mice brain than controls. That is, a more efficient transport of an optical probe (rhodamine 6G; abbreviated R6G) via the nasal route into mice brain, that is, deeper delivery of the optical probe was measured in comparison with either the corresponding, magnesium-free vesicular carrier or a conventional liposome carrier. Enhanced delivery was also noted following nasal delivery of insulin-labeled with fluorescein isothiocyanate (FITC) and near-infrared (NIR) fluorescently-labeled recombinant human epidermal growth factor (EGF).

Phospholipid magnesome has also been shown to have no negative effect of the nasal cavity in a rat model, e.g., mucosal epithelium remains intact with no indication of development of inflammation following application of phospholipid magnesome.

Additional experimental work supporting this invention includes a comparison of the analgesic activity of a painkiller delivered either from phospholipid magnesome or from a conventional liposome (analgesic activity of the test formulation/compounds is indicated by decrease in the frequency of writhes in the animal model). Very good writhing inhibition was achieved with the aid of phospholipid magnesome. Pharmacokinetic study (with ketoprofen as a drug model) demonstrates rapid absorption of the drug from phospholipid magnesome via the nasal route, as compared to significantly slower absorption from the oral administration of an equal dose of drug.

Lastly, the transition temperature (Tm) values reported below suggests that phospholipid magnesome consists of soft vesicles, i.e., vesicles exhibiting higher phospholipid fluidity as compared to corresponding conventional liposome.

In addition to the components already listed above, phospholipid magnesome may further include auxiliary agents, such as surfactants, preservatives, thickening agents, buffers, viscosity and absorption enhancing agents and agents capable of adjusting the pH and osmolarity of the formulation. Phospholipid magnesome may also include agents such as tolerance enhancers to reduce or prevent drying of the mucus membrane and to prevent irritation thereof.

Suitable preservatives that can be used with phospholipid magnesome include preservatives acceptable for nasal use, for example, benzyl benzalkonium salts.

Regarding buffers, phospholipid magnesome may include a buffer for maintaining the formulation at a pH of about. 7.0. The particular buffer, of course, can vary depending upon the particular nasal delivery system used, as well as the specific active molecule selected. Buffers that are suitable for use in the present invention include, for example, acetate, citrate, prolamine, carbonate and phosphate buffers and combinations thereof. The pharmaceutical formulations of the present invention may include a pH adjusting agent.

Regarding thickening agents, the viscosity of phospholipid magnesome can be maintained at a desired level using a pharmaceutically acceptable thickening agent. Thickening agents that can be added to the compositions of the present invention include for example, methyl cellulose, xanthan gum, tragacanth, adhesives, guar gum, carboxymethyl cellulose, hydroxypropyl cellulose, carbomer, polyvinyl alcohol, alginates, acacia, chitosans, mucoadhesive polymer-systems like poly(acrylates), cellulose derivatives, hyaluronic acid, hyaluronic acid derivatives, chitin, collagen, pectin, starch, poly(ethylene glycol), sulfated polysaccharides, carrageenan, Na-alginate, gelatine, pectin and combinations thereof. The desired concentration of the thickening agent will depend on the agent selected and the viscosity desired.

The invention also provides a nasally administrable composition comprising an active substance (in particular a physiologically/pharmaceutically active substance) in a carrier comprising glycol, phospholipids, water, at least one magnesium source as described above and at least one oil, e.g., vegetable oil such as hemp seed oil, sesame oil or olive oil, for example, up to 5% by weight.

The compositions of the invention can be prepared as liquid, viscous liquid or gel. It can also be incorporated into different dosage forms acceptable for the nasal route of administration, e.g., they may be incorporated into various nasal creams, nasal ointments, nasal suspensions and nasal gels in addition of course to nasal liquids.

As used herein, nasally administering or nasal administration includes administering the compositions into naristilles of the nose to the mucous membranes of the nasal passage or nasal cavity of the mammal. For example, the compositions of the invention can be delivered to the nasal cavity as drops; liquid delivered to the nasal cavity as non-aerosol spray (packaged in a bottle with an atomizer attachment, such as a pump-sprayer) or as an aerosol spray packed in a container under pressure to emit pressurized suspension, as described in detail in Remington's Pharmaceutical Sciences (16th edition, Chapters 83 and 92) Suitable devices [nasal sprays, metered-dose sprays, squeeze bottles, liquid droppers, disposable one-dose droppers, nebulizers, cartridge systems with unit-dose ampoules, single-dose pumps, bi-dose pumps, multiple-dose pumps] are of course commercially available from various sources. Regarding spray devices, it should be noted that both single (unit) dose or multiple dose systems may be used. Typically, a spray device comprises a bottle and a pump. Typically, the volume of liquid that is dispensed in a single spray actuation is in the range of from to 250 microliters/each nostril/single administration and the concentration of the active ingredient in the formulation may be readily adjusted such that one or more spray into the nostrils will comply with the dosage regimen. Administration of compositions of the present invention may also take place using a nasal tampon or nasal sponge containing the compositions.

The nasal administration may be used for systemic delivery of active compounds through the circulation or for CNS delivery for treating CNS-originating diseases or conditions.

A wide range of physiologic active substances can be administered via the nasal route with the aid of phospholipid magnesome to treat one or more of the following diseases and conditions: neurological disorder, muscular disturbances, ticks, brain, CNS, insomnia, pain, anxiety, migraine, glioma, epilepsy, astoglioma, cancer, acne, IBD, Chron's disease, loss of appetite, fear, distress, panic, tremor, multiple sclerosis, autism, Alzheimer, menopause, Parkinson, awakens, good mood, post-traumatic, alcoholic and nonalcoholic fatty liver, hysteria, seizure and types of encephalopathy, including hepatic-encephalopathy.

Phospholipid magnesome is, under a preferred aspect of the invention, suitable for enhancing the transport of hydrophilic compounds of any molecular size, inter alia, peptides, proteins and hydrophilic small molecule compounds (in the form of pharmaceutically acceptable salts), and nucleic acid based molecules such as antisense, iRNA, siRNA, micro RNA and anti-microRNA to the brain or systemically, as indicated by the results reported below. That is, peptides, amino acids, proteins and steroid hormones (e.g. insulin, insulin derivatives, insulin detemir, insulin monomeric, oxytocin, LHRH, LHRH analogues, adreno-corticotropic hormone, somatropin, leuprolide, calcitonin, parathyroid hormone, estrogens, testosterone, adrenal corticosteroids, megestrol, progesterone, sex hormones, growth hormones, growth factors, etc.)

But other active compounds can benefit from being delivered from phospholipid magnesome, for example cannabinoids and in particular derivatives of cannabinoids that have been rendered hydrophilic. The cannabinoid compound, either natural or synthetic, may be utilized in a solid form or in the form of an extraction concentrate, solvent extract, oil extract and oil solution, possibly surfactant-containing extracts and solutions. A non-limiting list of cannabinoids is given below:

$\Delta^9$-THC, available under the name dronabinol; and $\Delta^8$-THC.

CBD (chemical named 2-[3-methyl-6-(1-methylethenyl)-2-cyclohexen-1-yl]-5-pentyl-1,3-benzenedi-ol). The synthesis of CBD was described, for example, by Gaoni Y, Mechoulam R [Tetrahedron Letters. 26 (8): 1083-1086 (1985)]; and by Petilka et al. [Helv. Chim. Acta, 52:1102 (1969); and in J. Am. Chem. Soc., 87:3273 (1965)].

CBN (chemically named 6,6,9-trimethyl-3-pentyl-6H-dibenzo[b,d]pyran-1-ol). The synthesis of CBN was described by Novak et al., Tetrahedron Letters, 23:253 (19(32); and by Jesse A. Teske and Alexander Deiters *Org. Lett.,* 2008, 10 (11), pp 2195-2198.

Nabilone (chemically named: 3-(1,1-dimethylheptyl)-6, 6a,7,8,10,10a-hexahydro-1-hydroxy-6,6-dimethyl-9-H-dibenzo[b,d]pyran-9-one). The preparation of this synthetic cannabinoid is described, for example, in U.S. Pat. No. 3,968,125.

Levonantradol (chemically named: (−)-(6S,6aR, 9R,10aR)-5,6,6a,7,8, 9, 10,10a-octahydro-6-methyl-3-[(R)-1-meth-yl-4-phenylbutox]-1,9-phenanthridinediol 1-acetate. The preparation of this synthetic cannabinoid is described, for example, in U.S. Pat. Nos. 4,206,225, 4,232,018, 4,260, 764, 4,235,913, 4,243,674, 4,263,438, 4,270,005, and 4,283, 569.

(−)-HU-210 (chemically named: (−)-(3S,4S)-7-hydroxy-$\Delta^6$-tetrahydrocannabinol-1,1-dimethylhept-yl). The preparation of this synthetic cannabinoid can is found in U.S. Pat. Nos. 4,876,276 and 5,521,215.

(+)-HU-210 (chemically named: (+)-(3S,4S)-7-hydroxy-$\Delta^6$-tetrahydrocannabinol-1,1-dimethylhept-yl). The preparation of this synthetic cannabinoid is described in U.S. Pat. Nos. 4,876,276 and 5,521,215.

11-hydroxy-$\Delta^9$-THC, which can be prepared via the synthetic route described by Siegel et al., J. Org. Chem., 54:5428 (1989).

$\Delta^8$-tetrahydrocannabinol-11-oic acid, which is naturally occurring derivative and can be produced synthetically employing methods described in U.S. Pat. No. 6,162,829.

CP 55,940 (chemically named: 4-(1,1-dimethylheptyl)-2, 3' dihydroxy-6'alpha-(3-hydroxypropyl)-1',2',3',4',5',6'-hexahydrobiphenyl), which is commercially available from Tocris Cookson, Inc., Its preparation has been described; see for example U.S. Pat. Nos. 4,371,720 and 4,663,474.

R(+)-WIN 55,212-2 (chemically named: (R)-(+)-[2,3-dihydro-5-methyl-3-(4-morpholinylmethyl)-pyrrolo[1,2,3-de]-1-, 4-benzoxazin-6-yl]-1-naphthalenyl-methanone) is commercially available in the form of its mesylate salt from various manufacturers.

Crude herbal cannabis—in countries and jurisdictions where it is, or will become, legally allowed—can also be delivered using the composition of this invention.

It should be noted that the compositions of the invention is not limited to the delivery of a single active ingredient, and it may be used to provide combination therapy, that is, a second active ingredient could be added to the composition.

The following active ingredients (and of course, pharmaceutically acceptable salts thereof) can also be incorporated into phospholipid magnesome:

Antimalarial agents (e.g. artemisinin derivatives, dihydroartemisinin, artemotil, chloroquine, primaquine, doxycillin, quinine, aminoquinolines, cinchona alkaloids, antifolates, quinidine, melfoquine, halofantrine, lumefantrine, amodiaquine, pyronaridine, tafenoquine, artesunates, artemether, artemotil, biguanides, proguanil, chloroguanil, diaminopyrimidines, pyremethamine, trimethoprim, dapsone, sulfonamides, atovaquone, sulfadoxine-pyrimethamine, N-acetyl cysteine, piperaquine, DHA-piperaquine, lumefantrine, dermaseptins, bisphosphonates, quercitin etc. The drugs could be used alone or in combinations.

OTC drugs (e.g. antipyretics, anesthetics, cough suppressants, etc.)

Antiinfective agents

Antibiotics (e.g. penicillins, cephalosporins, macrolides, tetracyclines, aminoglycosides, anti-tuberculosis agents, doxycycline, ciprofloxacine, moxifloxacine, gatifloxacine, carbapenems, azithromycine, clarithromycine, erythromycine, ketolides, penems, tobramyicin, filgrastim, pentamidine, microcidin, clerocidin; amikacine, etc.)

Genetic molecules (e.g. Anti-sense oligonucleotides, nucleic acids, oligonucleotides, DNA, RNA, iRNA, siRNA, micro RNA and anti-microRNA)

Anti-cancer agents (e.g. anti-proliferative agents, anti-vascularization agents, taxol, etopside, cisplatin, etc.)

Anti-protozoal agents

Antivirals (e.g. acyclovir, gancyclovir, ribavirin, anti-HIV agents, anti-hepatitis agents, famciclovir, valaciclovir, didanosine, saquinavir, ritonavir, lamivudine, stavudine, zidovudine, etc.)

Anti-inflammatory drugs (e.g. NSAIDs, steroidal agents, cannabinoids, leukotriene-antagonists, tacrolimus, sirolimus, everolimus, etc.)

Anti-allergic molecules (e.g. antihistamines, fexofenadine)

Bronchodilators

Vaccines and other immunogenic molecules (e.g. tetanus toxoid, reduced diphtheria toxoid, acellular pertussis vaccine, mums vaccine, smallpox vaccine, anti-HIV vaccines, hepatitis vaccines, pneumonia vaccines, influenza vaccines, TNF-alpha-antibodies etc.)

Anesthetics, local anesthetics.
Antipyretics (e.g. paracetamol, ibuprofen, diclofenac, aspirin, etc.)
Agents for treatment of severe events such cardiovascular attacks, seizures, hypoglycemia, etc.
Afrodisiacs from plants or synthetics
Anti-nausea and anti-vomiting.
Immunomodulators (immunoglobulins, etc.)
Cardiovascular drugs (e.g. beta-blockers, alpha-blockers, calcium channel blockers, etc.)
Peptide and steroid hormones (eg. insulin, insulin derivatives, insulin detemir, insulin monomeric, oxytocin, LHRH, LHRH analogues, adreno-corticotropic hormone, somatropin, leuprolide, calcitonin, parathyroid hormone, estrogens, testosterone, adrenal corticosteroids, megestrol, progesterone, sex hormones, growth hormones, growth factors, etc.)
Peptide and protein related drugs (e.g. amino acids, peptides, polypeptides, proteins)
Vitamins (e.g. Vit A, Vitamins from B group, folic acid, Vit. C, Vit D, Vit E, Vit K, niacin, derivatives of Vit D, etc.)
Autonomic Nervous System Drugs
Fertilizing agents
Antidepressants (e.g. buspirone, venlafaxine, benzodiazepins, selective serotonin reuptake inhibitors (SSRIs), sertraline, citalopram, tricyclic antidepressants, paroxetine, trazodone, lithium, bupropion, sertraline, fluoxetine, etc.)
Agents for smoking cessation (e.g. bupropion, nicotine, etc.)
Agents for treating alcoholism and alcohol withdrawal
Lipid-lowering agents (e.g. inhibitors of 3 hydroxy-3-methylglutaryl-coenzyme A (HMG-CoA) reductase, simvastatin, atrovastatin, etc.)
Drugs for CNS or spinal cord (benzodiazepines, lorazepam, hydromorphone, midazolam, Acetaminophen, 4'-hydroxyacetanilide, barbiturates, anesthetics, etc.)
Anti-epilepsic agents (e.g. valproic acid and its derivatives, carbamazepin, etc.)
Angiotensin antagonists (e.g. valsartan, etc.)
Anti-psychotic agents and anti-schizophrenic agents quetiapine, risperidone)
Agents for treatment of Parkinsonian syndrome (e.g. L-dopa and its derivatives, trihexyphenidyl, etc.)
Anti-Alzheimer drugs (e.g. cholinesterase inhibitors, galantamine, rivastigmine, donepezil, tacrine, memantine, N-methyl D-aspartate (NMDA) antagonists).
Agents for treatment of non-insulin dependent diabetes metformine,
Agents against erectile dysfunction (e.g. sildenafil, tadalafil, papaverine, vardenafil, PGE1, etc.)
Prostaglandins
Agents for bladder dysfunction (e.g. oxybutynin, propantheline bromide, trospium, solifenacin succinate etc.)
Agents for treatment menopausal syndrome (e.g estrogens, non-estrogen compounds, etc.)
Agents for treatment hot flashes in postmenopausal women
Agents for treatment primary or secondary hypogonadism (e.g. testosterone, etc.)
Cytokines (e.g. TNF, interferons, IFN-alpha, IFN-beta, interleukins etc.)
CNS stimulants
Muscle relaxants
Anti paralytic gas agents
Appetite stimulators/depressors (e.g. cannabinoids, etc.)
Gastrointesinal absorption modifiers
Narcotics and Antagonists (e.g. opiates, oxycodone etc.)
Painkillers (opiates, endorphins, tramadol HCl, codein, NSAIDs, gabapentine, fentanil and pharamaceutically acceptable salts thereof etc.)
Hypnotics (Zolpidem, benzodiazepins, barbiturates, ramelteon, etc.)
Histamines and Antihistamines
Antimigraine Drugs (e.g. imipramine, propranolol, sumatriptan, eg.)
Diagnostic agents (e.g. Phenolsulfonphthalein, Dye T-1824, Vital Dyes, Potassium Ferrocyanide, Secretin, Pentagastrin, Cerulein, etc.)
anti-inflammatory drugs
ADHD related medication (e.g. methylphenidate, dexmethylphenidate, dextroamphetamine, d- and l-amphetamin racemic mixture, pemoline, etc.)
Diuretic agents
Anti-osteoporotic agents (e.g. bisphosphonates, aledronate, pamidronate, tirphostins, etc.)
Drugs for treatment of asthma
drugs for post trauma, crisis, anxiety treatment
Anti-Spasmotic agents (e.g. papaverine, etc.)
Agents for treatment of multiple sclerosis and other neurodegenerative disorders (eg. mitoxantrone, glatiramer acetate, interferon beta-1a, interferon beta-1b, etc.)
Plant derived agents from leave, root, flower, seed, stem or branches extracts.
Anti anxiety drugs.

The experimental work reported below shows that the carrier of the invention can be used for delivery to the brain via the nasal route of pharmaceutically active agents spanning a wide range of molecular weight and physiochemical properties, e.g.:
   large molecules (e.g., molecular weight >1000 g/mol) such as peptide hormones (insulin, oxytocin) and proteins.
   small molecules, for example, with molecular weights up 500 g/mol including compounds bearing hydrophilic functional groups (carboxylic acid, hydroxyl) and salt-forming groups, e.g., compounds administered as acid addition salts, such as tramadol hydrochloride (analgesic), butorphanol tartrate (opioid); rizatriptan benzoate (antimigraine) safinamide mesylate (anti-Parkinson); and other small molecules such as mannitol, ketoprofen and brotizolam, and also cannabinoids (CBD, CBN, THC or mixtures thereof).

Accordingly, specific aspects of the invention include compositions comprising a pharmaceutically active agent selected from:
   an analgesic, antimigraine and/or antipyretic agent (e.g., tramadol, ketoprofen, rizatriptan and pharmaceutically acceptable salts thereof);
   an opioid (e.g., butorphanol and pharmaceutically acceptable salts thereof);
   an anti-Parkinson drug (e.g., safinamide and pharmaceutically acceptable salts thereof);
   a sedative and/or hypnotic drug (e.g., brotizolam or a pharmaceutically acceptable salt thereof);
   a peptide or a polypeptide peptide hormone selected from the group consisting of insulin and oxytocin, or bacitracin);
   a cannabinoid or a mixture of cannabinoids (CBD, THC, CBN or a mixture thereof).

It should be noted that concentration of the active agent in the composition of the invention may vary broadly, from 0.01 to 20% by weight.

Additional aspect of the invention relates to a method of administering an active substance to a mammal in need thereof, comprising intranasal administration of a composition comprising a therapeutically effective amount of the active substance (e.g., an analgesic, antimigraine and/or antipyretic agents; an opioid; an anti-Parkinson drug; a sedative and/or hypnotic drug; peptide or a polypeptide; a cannabinoid) in a magnesium-containing vesicular carrier that contains glycol, phospholipids, water and at least one magnesium source.

Use of a vesicular carrier that contains glycol, phospholipids, water and at least one magnesium source as described herein (e.g., monohydroxy aliphatic alcohol-free carrier), for intranasal administration of pharmaceutically active agents for systemic delivery or CNS (central nervous system) delivery, is another aspect of the invention.

Owing to its ability to offer a rapid onset of an analgesic effect, the composition of the invention is especially useful in a method for pain relief, the method comprising the intranasal administration to a patient of a composition comprising a carrier and therapeutically effective amount of an active substance selected from the group consisting of an analgesic, an opioid, an antimigraine agent and an anti-inflammatory, wherein the carrier in a magnesium-containing vesicular carrier comprising glycol, phospholipids, water and at least one magnesium source.

We have also found that the pharmaceutically active agent pramipexole could be administered intranasally with the aid of the magnesium-containing vesicular carrier of the invention to achieve efficient therapeutic effect. Pramipexole a dopamine agonist drug with selective activity at D2/D3-receptors. It is approved as mono and adjunctive therapy for treatment of motor symptoms in patients with Parkinson's disease. Currently pramipexole was administrated orally in immediate and extended release tablet formulations. Transdermal delivery of pramipexole was described in U.S. Pat. No. 5,112,842. Little has been reported on the nasal delivery of pramipexole, e.g., pramipexole was loaded on chitosan nanoparticles [raj et. al., In J Biol Macromol 2018 1; 109:27-35].

The commercial form of pramipexole is its dihydrochloride salt (of the (S)-enantiomer). The term pramipexole, as used herein, is directed to 2-amino-6-propylamino-4,5,6,7-tetrahydrobenzothiazole, its (S)-enantiomer, and pharmaceutically acceptable salts thereof, such as the dihydrochloride salt. However, it also includes the (R)-enantiomer and mixtures of both. Utilities of the (R)-enantiomer are reported in U.S. Pat. No. 7,157,480.

Studies reported herein indicate greatly improved results of behavioral testing in Parkinson's mice model following nasal administration of pramipexole by the composition of the invention. That is, significant reversal of reserpine-induced locomotor impairment, reserpine-induced ptosis and reserpine-induced catalepsy compared to pramipexole oral solution. Pramipexole used in the studies reported below was pramipexole dihydrochloride monohydrate.

Another aspect of the invention is therefore a method of treating Parkinson's disease, motor symptoms associated with Parkinson's disease, including treating impaired locomotion in Parkinson's disease patients, Parkinsonism, and other pramipexole-treatable diseases, such as restless legs syndrome and other diseases and conditions affected by dopamine modulation), which method comprises administering intranasally, to a mammal in need thereof, a pharmaceutical composition comprising pramipexole and a vesicular carrier.

The invention further provides a method for treating impaired locomotion, comprising administering intranasally, to a patient in need thereof, a pharmaceutical composition comprising anti-Parkinson drug (such as pramipexole), in a vesicular carrier.

The term vesicular carrier, as used herein in connection with the administration of pramipexole, is a carrier comprising phospholipids, water and one of monohydroxy/dihydroxy alcohol, or both. However, the preferred vesicular carrier is the magnesium-containing vesicular carrier disclosed herein, namely, Phospholipid Magnesome, which comprises glycol, phospholipids, water and at least one magnesium source (and is generally free of monohydroxy alcohol).

Accordingly, another aspect of the invention is a nasally administrable composition comprising pramipexole in magnesium-containing vesicular carrier, said carrier comprising glycol, phospholipids, water and at least one magnesium source, e.g., from 0.1 to 2% by weight pramipexole (e.g., from 0.5 to 1.0%), from 5 to 50% by weight propylene glycol (e.g., from 10 to 30%), from 0.2 to 10% by weight phospholipids (e.g., from 1 to 5%), not less than 20% by weight water (e.g., not less than 50%) and not less than 0.01% magnesium source (e.g., from 0.05 to 1.0% by weight magnesium salt such as $MgSO_4$). The composition may further contain an antioxidant such as vitamin E and an alkaline agent such as sodium hydroxide.

The therapeutically effective amount of pramipexole is generally from 0.1 to 5 mg (e.g., from 0.001 to 0.05 mg/kg of body weight). Experimental work reported below indicates that nasally-administrable compositions containing from 0.5 to 1.0% by weight of pramipexole are readily formulated, such that administration of one or more applications (e.g., spray, drops, gel) into the nostrils 1 to 6 times per day will comply with the dosage regimen.

Lastly, it should be noted that the nasal vesicular composition without an added drug/pharmaceutically active compound, can also be used, e.g., for ONS effect. The carrier of the invention may contain high concentration of magnesium, useful for such purpose. Hence nasally administrable vesicular composition comprising glycol, phospholipids, water and at least one magnesium source, wherein the composition is devoid of an active substance, constitutes another aspect of the invention. Concentration ranges for the components are as previously indicated.

In the drawings:

FIG. 1: Three-dimensional micrographs of the olfactory region for mice brain treated with R6G at a dose of 10 mg/kg from phospholipids magnesome, water solution and Liposome. Height: 589 µm, width: 589 µm, depth: 606 µm, lens ×20 (A1-MP microscope NIKON-Japan).

Figure 2:
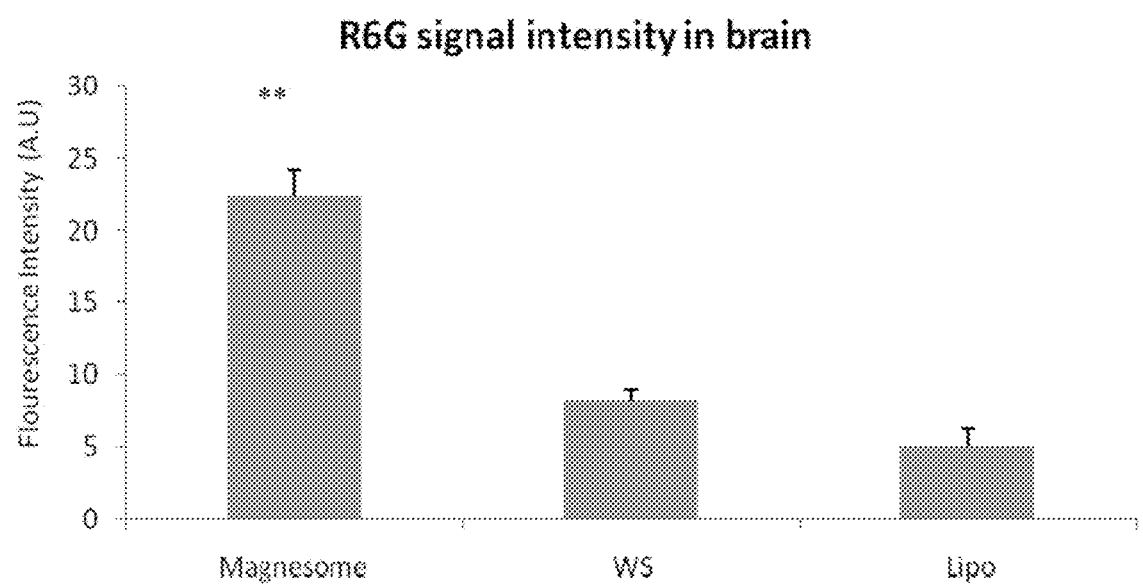

FIG. 2: a bar diagram showing fluorescent intensity (A.U.) in the olfactory region of mice brain at 10 min after treatment with R6G at a dose of 3 mg/kg in phospholipids magnesome, water solution and Liposome; Mean±SD. Auto fluorescence was subtracted. **P value<0.01 considered very significant.

Figure 3:
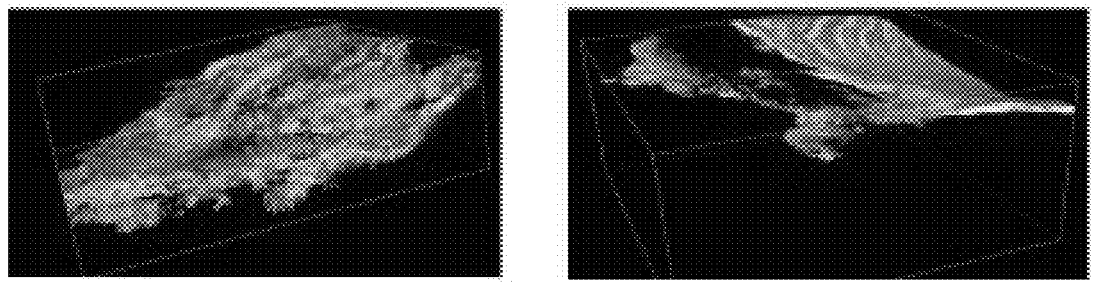

FIG. 3: Three-dimensional micrographs of the olfactory region for mice brain treated with R6G at a dose of 10 mg/kg from phospholipid magnesome vs. soft vesicles. Height: 979 µm, width: 979 µm, depth: 507 µm, lens ×20 (A1-MP microscope NIKON-Japan).

Figure 4:
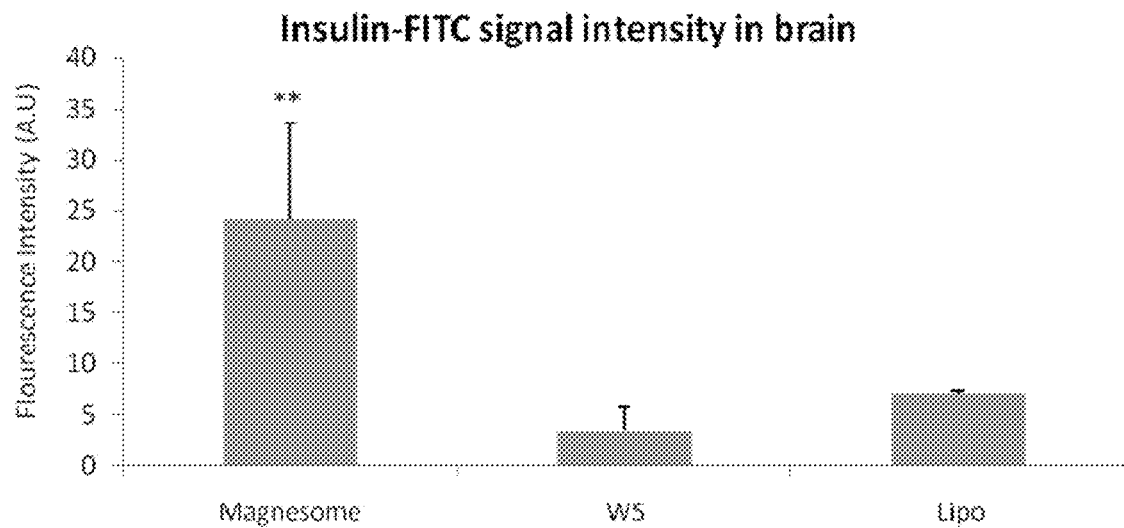

FIG. 4: a bar diagram showing fluorescent intensity (A.U.) in the olfactory region of mice brain at 10 min after treatment with Insulin-FITC at a dose of 1 mg/kg in phospholipids magnesome, WS and Lipo; Mean±SD. Auto fluorescence was subtracted. **P value<0.01 considered very significant.

Figure 5:
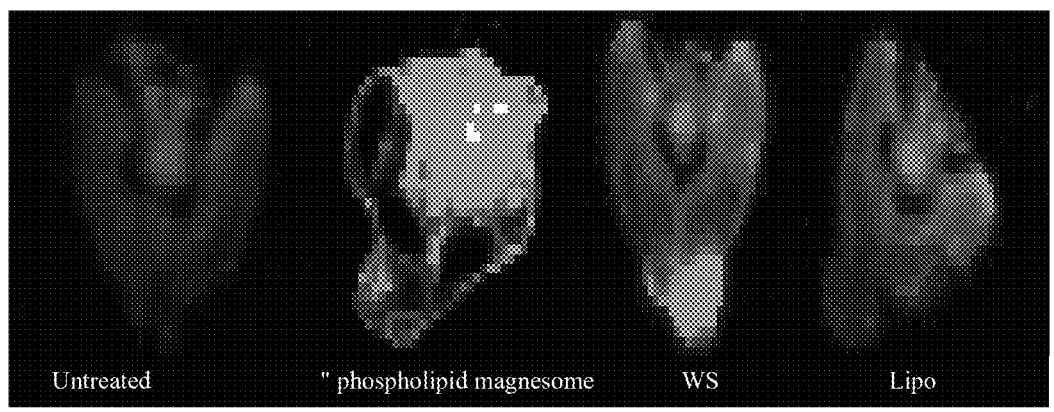

FIG. 5: NIR images for mice brains treated with EPG IRDye 800CW at a dose 1 mg/Kg from phospholipid magnesome as compared to water solution and liposome.

Figure 6:
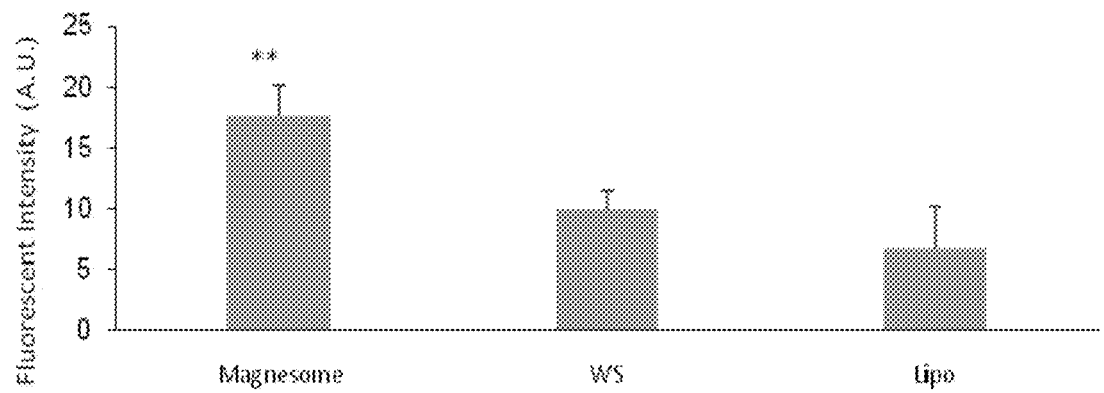

FIG. 6: a bar diagram showing fluorescent intensity (A.U.) in the olfactory region of mice brain at 10 min after treatment with EGF-IRDye 800CW at a dose of 1 mg/kg in phospholipids magnesome, as compared to water solution and liposome; Mean±SD. Auto fluorescence was subtracted. **P value<0.01 considered very significant.

Figure 7:
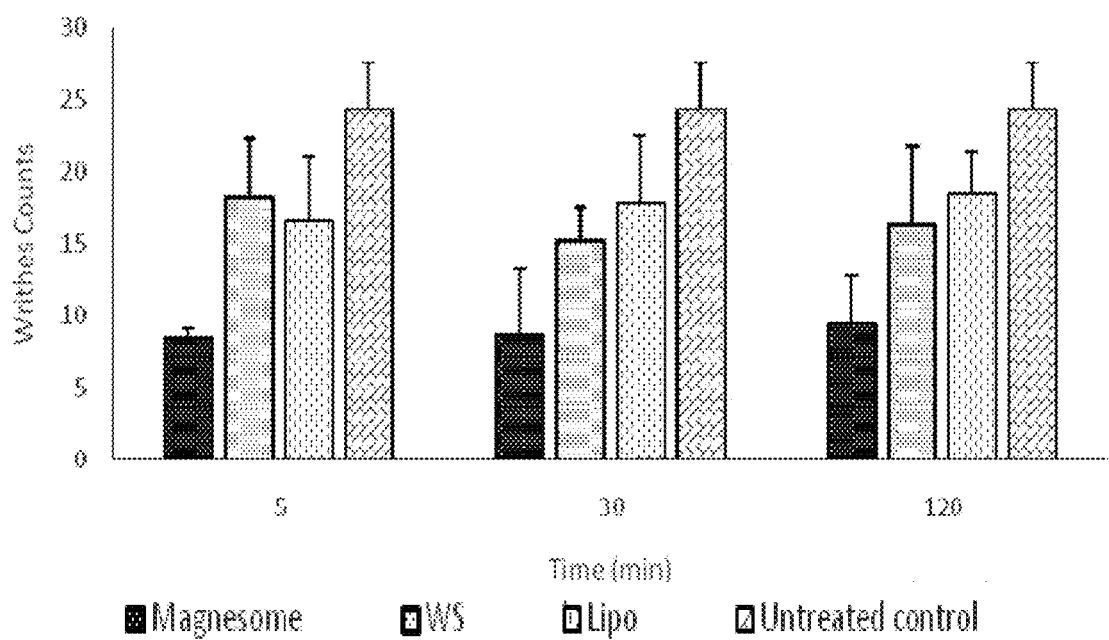
Figure 8A:
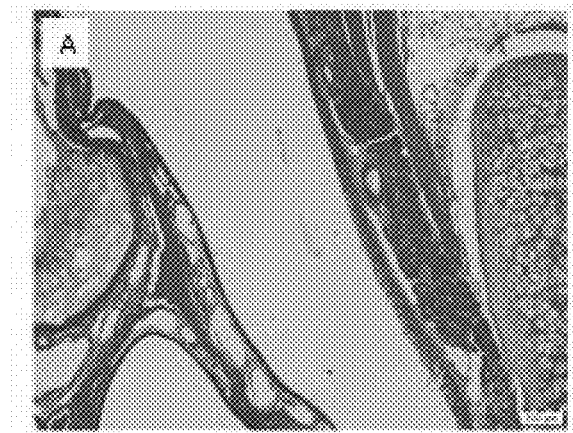
Figure 8B:
Figure 8C:
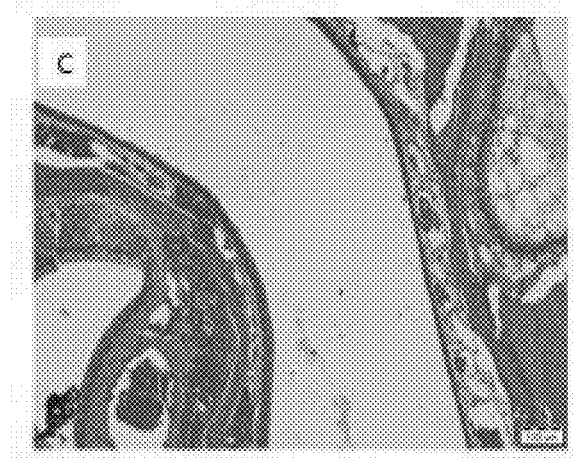
Figure 8D:
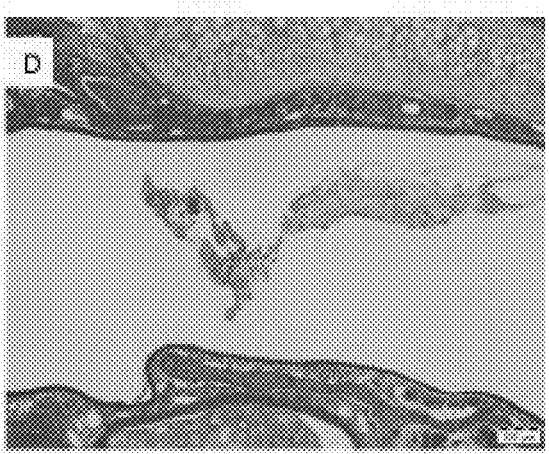

FIG. 7: a bar diagram showing the writhing counts for mice treated with Oxytocin at a dose of 0.4 mg/kg phospholipid magnesome, WS, Lipo and Untreated control 5, 30 and 120 min prior to IP injection of acetic acid; Mean±SD. P<0.05 for phospholipid magnesome vs. untreated, WS and Lipo 5 min. P<0.01 for phospholipid magnesome vs. untreated, WS and Lipo at 30 and 120 min time points.

FIGS. 8A-8D: Representative micrographs of nasal cavities excised from rats that (A) received no treatment or treated with (B) phospholipid Magnesome, (C) NS and (D) SLS nasal solution.

Figure 9A:
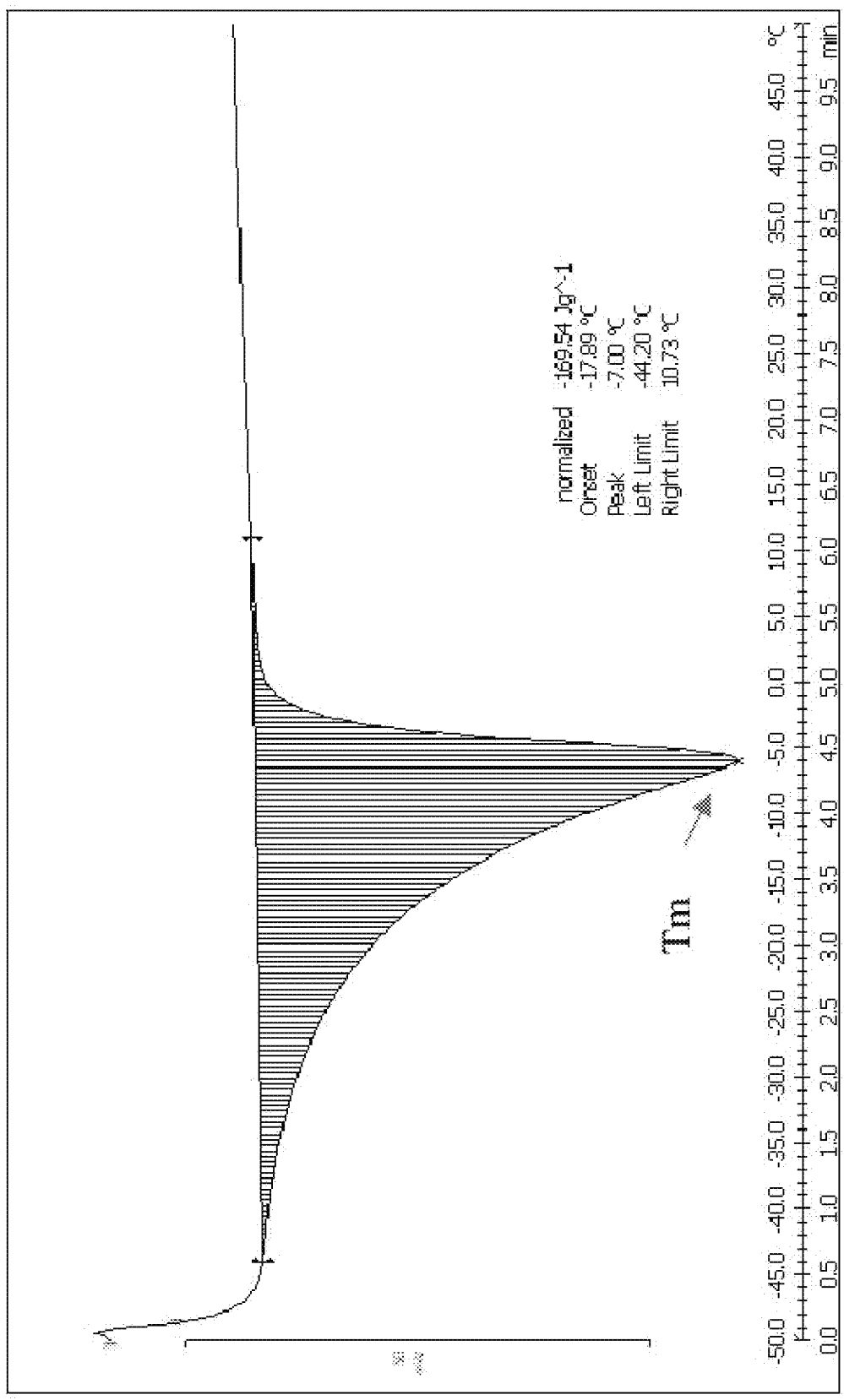
Figure 9B:
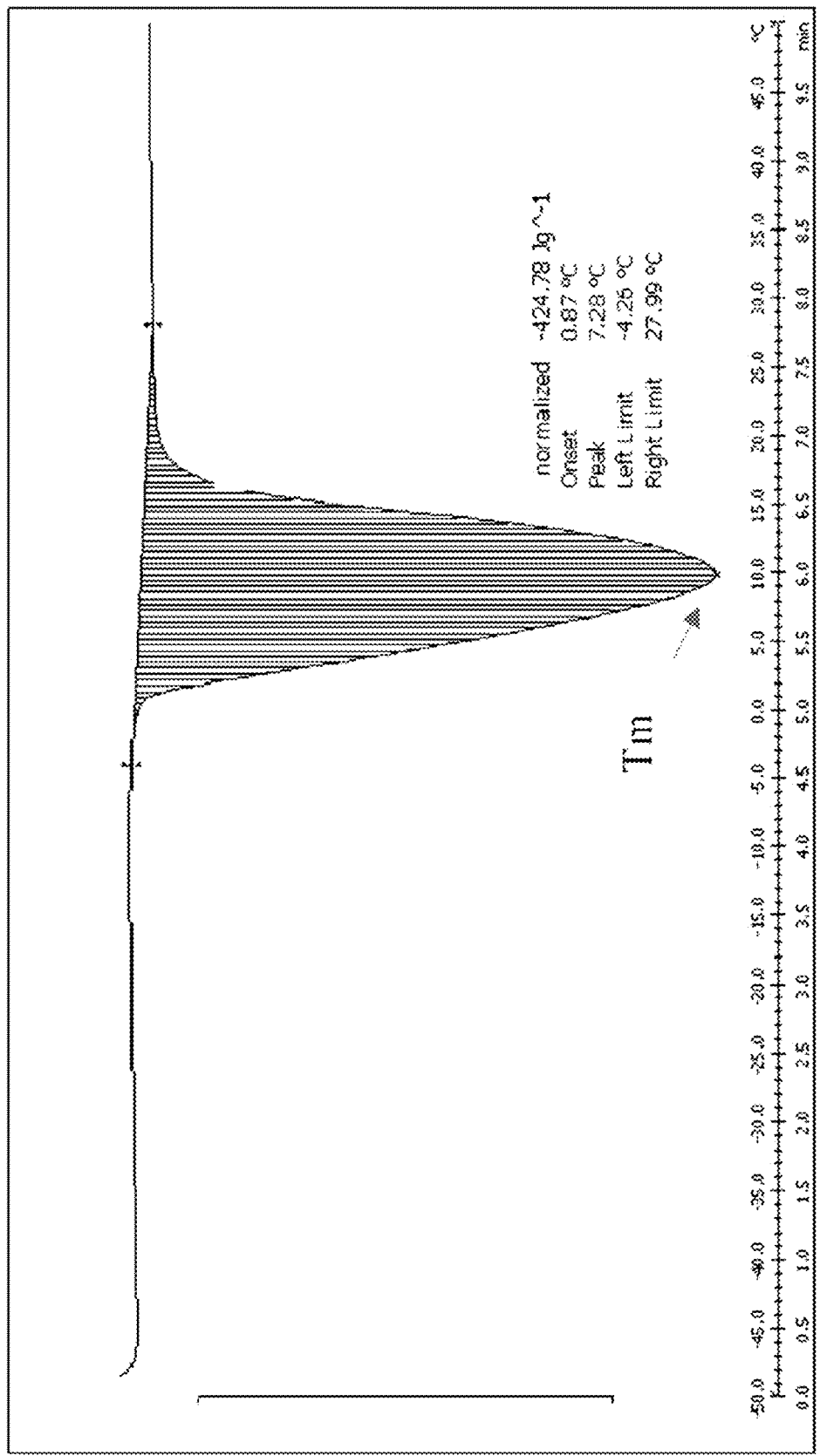

FIGS. 9A-9B: DSC thermograms for (A) phospholipids magnesome, (B) liposome obtained by Mettler Toledo DSC-1 STAR system (China).

Figure 10:
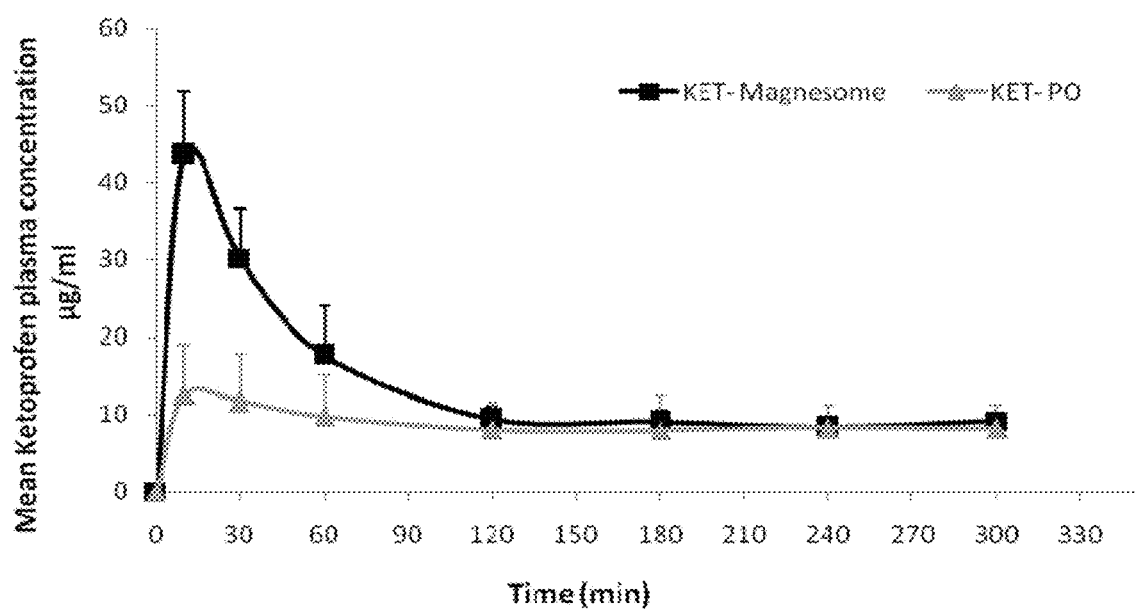

FIG. 10: a graph showing the pharmacokinetic profile of Ketoprofen in plasma following nasal administration of Ketoprofen from the composition of the invention vs. Ketoprofen oral administration, each at a dose of 14 mg/Kg. Results (mean±SD) **P<0.01, very significant at 10 min, and 30 min.

Figure 11:
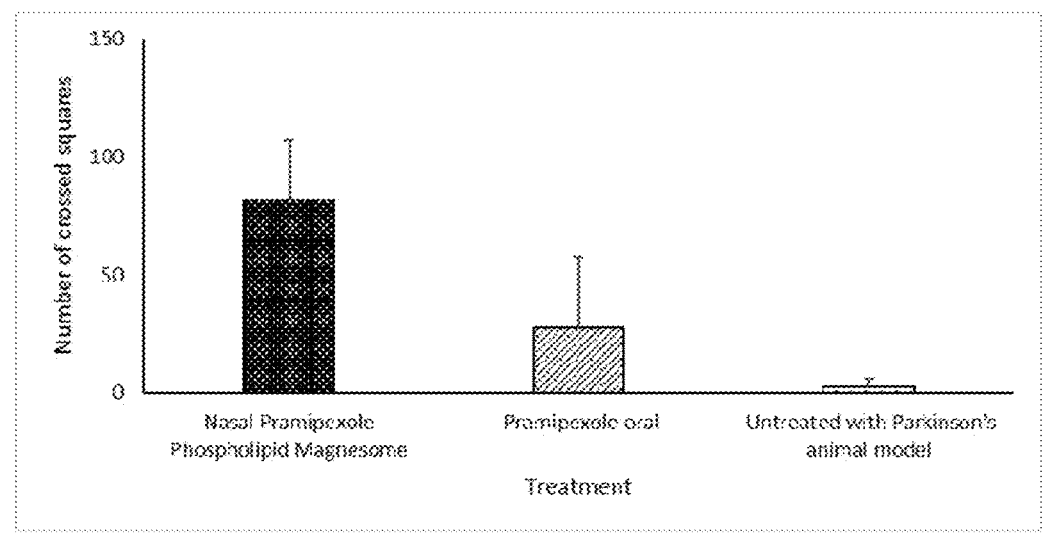

FIG. 11: Number of squares crossed in the open field test by Parkinson's mice treated with: ■ Nasal Pramipexole Phospholipid Magnesome (n=6); ▨ Oral Pramipexole solution (n=4) and ▫ untreated animals (n=5), (Mean±SD). p<0.001 for Pramipexole Phospholipid Magnesome vs. untreated control, p<0.01 for Pramipexole Phospholipid Magnesome vs. oral, p>0.05 (considered not significant) for Pramipexole oral vs. untreated control by one-way ANOVA.

Figure 12:
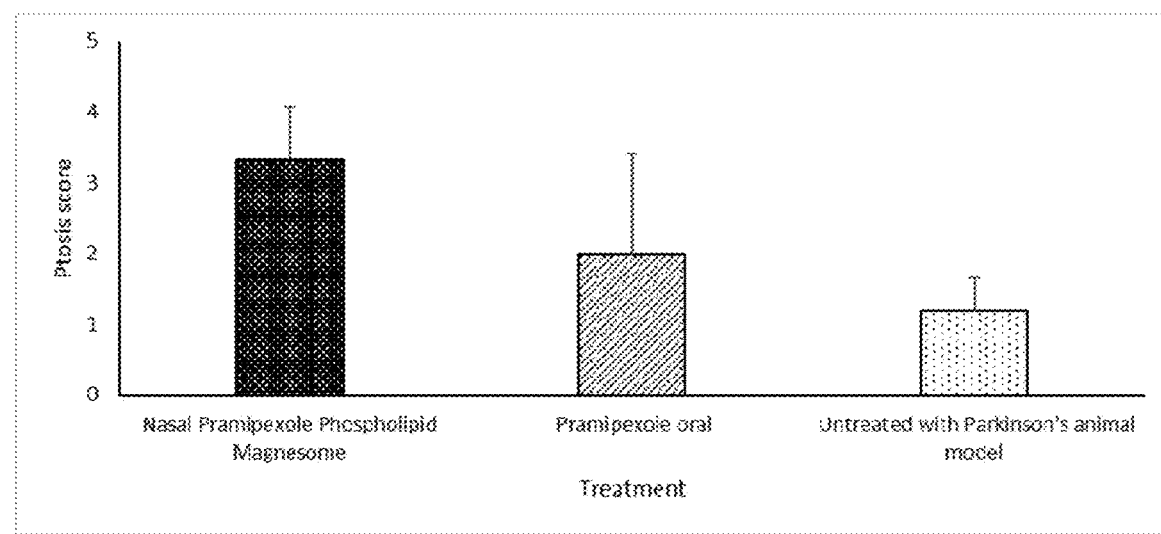

FIG. 12: Ptosis scores for Parkinson's mice model treated with: ■ Nasal Pramipexole Phospholipid Magnesome (n=6); ▨ Oral Pramipexole Solution (n=4) and ▫ untreated animals (n=5), (Mean±SD). p<0.01 for Pramipexole Phospholipid Magnesome vs. untreated control, p>0.05 for Pramipexole nasal vs. oral and oral vs. untreated, by one-way ANOVA.

Figure 13:
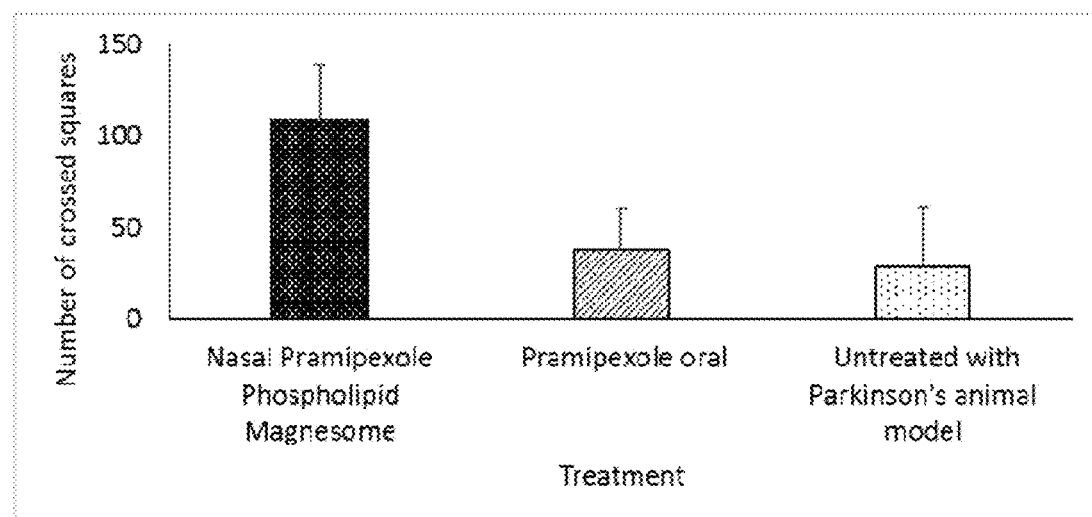

FIG. 13: Number of squares crossed in the open field test by Parkinson's mice model treated with: ■ Nasal Pramipexole Phospholipid Magnesome; ▨ Oral Pramipexole solution and ▫ untreated animals (n=7/group), (Mean±SD). p<0.001 for Pramipexole Phospholipid Magnesome vs. untreated control, p<0.01 for Pramipexole Phospholipid Magnesome vs. oral, p>0.05 (considered not significant) for Pramipexole oral vs. untreated control by one-way ANOVA.

Figure 14:
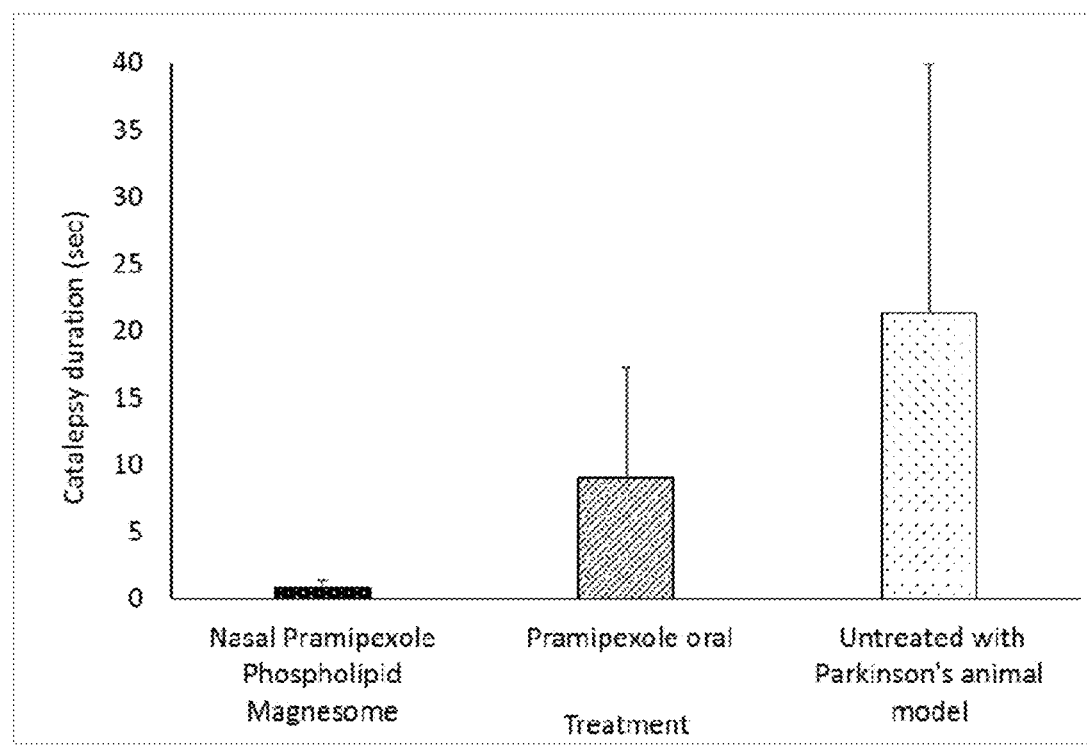

FIG. 14. Catalepsy duration measured by bar test for Parkinson's mice model treated with: ■ Nasal Pramipexole Phospholipid Magnesome; ▨ Oral Pramipexole solution and ▫ untreated animals (n=7/group), (Mean±SD). p<0.001 for Pramipexole Phospholipid Magnesome vs. untreated control, p<0.01 for Pramipexole Phospholipid Magnesome vs. oral, p>0.05 (considered not significant) for Pramipexole oral vs. untreated control by two tail Mann-Whitney test.

Figure 15:
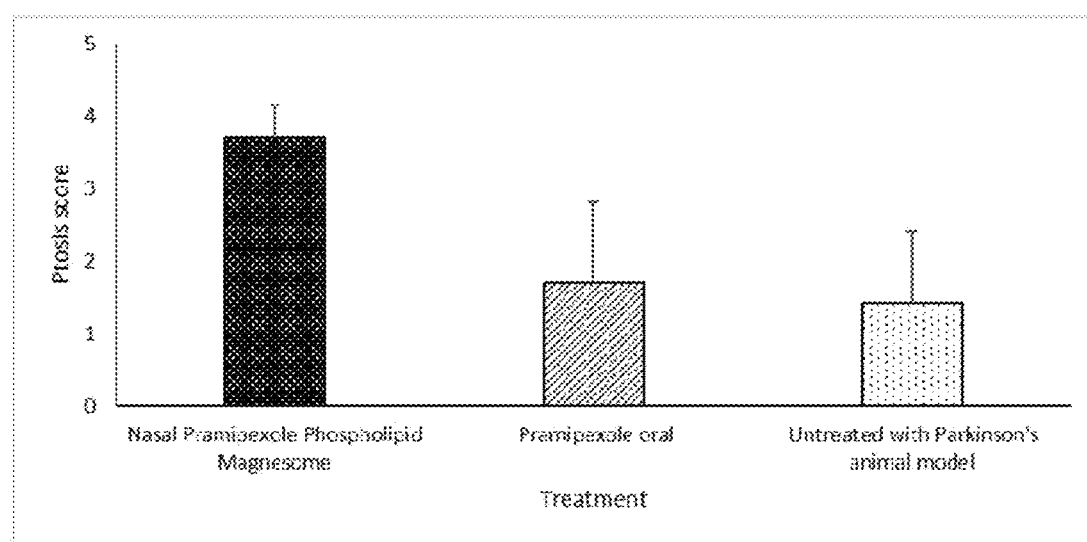

FIG. 15. Ptosis scores for Parkinson's mice model treated with: ■ Nasal Pramipexole Phospholipid Magnesome; ▨ Oral Pramipexole solution and ▫ untreated animals (n=7/group), (Mean±SD). p<0.001 for Pramipexole Phospholipid Magnesome vs. untreated control, p<0.01 for nasal vs. oral and p>0.05 for oral vs. untreated, by one-way ANOVA.

EXAMPLES

Abbreviations used in the examples:
PL—Phospholipid
PG—Propylene Glycol
WS—Water solution
DDW—Double distilled water
ETOH—Ethanol
HSO—Hemp Seed Oil
SO—Sesame oil
Lipo—Liposome The following materials were used: Magnesium Sulfate, anhydrous from J.T. Baker, USA; Phospholipon 90 G—Lipoid, Phospholipid GmbH, Germany; Propylene Glycol—Tamar, Israel and Vitamin E Acetate—Tamar, Israel.

Example 1

Nasal Delivery to Brain

Nasal delivery of R6G in the composition of the invention to the olfactory region of mice brain visualized by a Multiphoton Microscope (A1-MP microscope NIKON-Japan).

Part I

Nine female C57B1/6J mice (8-9 weeks), were divided equally into 3 groups of administration. The following formulations were prepared:

| | Phospholipid magnesome (% w/w) | Water solution % w/w | Liposome % w/w |
|---|---|---|---|
| R6G | 1 | 1 | 1 |
| PL | 3 | — | 3 |
| PG | 15 | — | — |
| Sodium alginate | 0.6 | — | 0.6 |
| Magnesium sulfate | 0.03 | — | — |
| DDW | To 100 | To 100 | To 100 |

Preparation: PL was dissolved in PG, R6G was added and then 20% of the total DDW amount was added, through mixing. In a separate vessel, Sodium Alginate was dispersed in 10% of the total amount of DDW and mixed with Magnesium Sulfate aqueous solution (10 mg/ml). The PL solution was then added to the alginate gel through mixing with an overhead stirrer (Heidolph digital 200 RZR-2000, Germany), then the remaining DDW was added.

R6G was administered nasally to mice from the three above formulations at a dose of 10 mg/kg animal (~0.2 mg\20 µl/mouse). Ten minutes after treatments, the animals were sacrificed, the brains were removed, washed with normal saline and examined by the Multiphoton Microscope using the following conditions: excitation λ 850 nm, field of image of 589×589×606 nm (width×height×depth), lens ×60 laser, intensity 5%, scanning 512, scan speed 0.5, line skipping 2, Luts1500 and zoom1. The fluorescence intensity of the probe (arbitrary units A.U.) in the olfactory region in brain was further assessed using Image Pro-Plus software.

The micrographs are presented in FIG. 1 (left: phospholipid magnesome; middle: water solution; right: liposome). FIG. 2 is a bar diagram showing the fluorescent intensity. The micrographs of Multiphoton Microscopic examination and the semi-quantification showed that higher fluorescent signals are found in the olfactory region in the groups treated with phospholipid magnesome containing R6G relative to different control nasal compositions Water Solution (WS) and Liposome (Lipo). It is worthy to notice that the fluorescence intensity in the WS group was apparently higher (yet not statistically significant) than that achieved in the animals receiving Lipo treatment.

These results point towards the efficiency of phospholipid magnesome to improve the hydrophilic probe delivery to the examined region in the brain.

Part II

In this part, the effect of pospholipid magnesome was evaluated in comparison with a composition without magnesium.

Female C57B1/6J mice (8-9 weeks), were divided into 2 groups of administration. The following formulations were prepared:

|  | Phospholipid magnesome (% w/w) | No Mg % w/w |
| --- | --- | --- |
| R6G | 1 | 1 |
| PL | 3 | 3 |
| PG | 15 | 15 |
| Magnesium sulfate | 0.03 | — |
| DDW | To 100 | To 100 |

The administered dose and the experimental procedure was performed as described in Part I of this example.

FIG. 3 shows the three-dimensional micrographs. The results of this part of the experiment show deeper delivery of R6G into the examined brain region. The semi quantification indicated a fluorescence of 13.2 A.U. to the phospholipid magnesome as compared to 8.0 A.U. for the soft vesicles, such results pointing towards the superiority of phospholipid magnesome as carrier for brain delivery of drugs.

Example 2

Nasal Delivery of Insulin-FITC to Brain

Nasal delivery of Insulin FITC to the olfactory region in mice brain from the composition of the invention and two control compositions, examined by a Multiphoton Microscope (A1-MP microscope NIKON-Japan).

Nine female C57B1/6J mice (8-9 we were divided equally into groups of administration. The following formulations were prepared.

|  | Phospholipid magnesome (% w/w) | Water solution % w/w | Liposome % w/w |
| --- | --- | --- | --- |
| Insulin FITC | 0.1 | 0.1 | 0.1 |
| PL | 3 | — | 3 |
| PG | 15 | — | — |
| Sodium alginate | 0.6 | — | 0.6 |
| Magnesium sulfate | 0.03 | — | — |
| DDW | To 100 | To 100 | To 100 |

Preparation: PL was dissolved in PG, Insulin FITC was added then 20% of the total DDW amount was added, through mixing. In a separate vessel, Sodium Alginate was dispersed in 10% of the total amount of DDW and mixed with Magnesium Sulfate aqueous solution (10 mg/ml). The PL solution was then added to the alginate gel through mixing and then the remaining DDW was added.

Insulin FITC was administered nasally to mice from the three formulations at a dose of 1 mg/kg animal (~0.02 mg\20 μl/mouse). Ten minutes after treatments, the animals were sacrificed, the brains were removed, washed with normal saline and examined by the Multiphoton Microscope using the following conditions: excitation λ of 860 nm, field 58.6×58.6×30.6 nm (width×height×depth), lens ×20, laser intensity 11.1%, scanning 512, scan speed 0.5, no line skipping, Luts: 1000 and zoom 9.9. The fluorescence intensity of the probe (arbitrary units A.U.) in the olfactory region in brain was further assessed using Image Pro-Plus software.

Multiphoton imaging of the olfactory region following Insulin-FITC administration in phospholipid magnesome indicates the presence of augmented fluorescent signal in this group relative to controls (micrographs are not shown). Semi-quantification of the fluorescence signals gave fluorescent intensities of ~24 A.U. in brain section of animals treated with phospholipid magnesome containing Insulin-FITC as compared to 3.4 and 7.0 A.U. for the controls WS and Lipo, respectively, as shown in the bar diagram of FIG. 4.

Example 3

Nasal Delivery of EGF-IRDye 800CW to Brain

Nasal delivery of EGF-IRDye 800CW to brain of mice from phospholipid magnesome as compared with two controls, was examined by Odyssey® Infrared Imaging System (LI-OCR, USA).

Twelve female C57B1/6J mice (8-9 weeks) were divided equally into 3 groups of administration and Untreated Control group. The following formulations were prepared.

|  | Phospholipid magnesome (% w/w) | Water solution % w/w | Liposome % w/w |
| --- | --- | --- | --- |
| EGF-IRDye 800CW | 0.1 | 0.1 | 0.1 |
| PL | 3 | — | 3 |
| PG | 15 | — | — |
| Sodium alginate | 0.6 | — | 0.6 |
| Magnesium sulfate | 0.03 | — | — |
| DDW | To 100 | To 10 0 | To 100 |

Preparation: PL was dissolved in PG, EGF-IRDye 800CW was added and then 20% of the total DDW amount was added, through mixing. In a separate vessel, Sodium Alginate was dispersed in 10% of the total amount of DDW and mixed with Magnesium Sulfate aqueous solution (10 mg/ml). The PL solution was then added to the alginate gel through mixing, then the remaining DDW was added.

EGF-IRDye 800CW was administered nasally to mice from the three formulations at a dose of 1 mg/kg animal (~0.02 mg\20 μl/mouse). Ten minutes after treatments, the animals were sacrificed; brains were removed, washed with normal saline and observed under the imaging system. The scanning was performed using offset 3, resolution 339.6 μm, channel 800 nm and intensity 3.

The NIR images (FIG. 5; from left to right: untreated group, phospholipid magnesome-treated group; water solution-treated group and liposome-treated group) and their semi-quantification (FIG. 6, in the form of a bar diagram) indicate the presence of the labeled peptide signal in brain tissues following nasal administration from various systems as compared to Untreated Control. FIG. 5 shows that following administration from phospholipid magnesome, EGF-IRDye 800CW accumulated in the cerebrum and in the olfactory bulb with remarkable accumulation in the cerebrum. The administration from water solution lead to peptide accumulation in the olfactory bulb (FIG. 5). The fluorescent signals calculated to be 19.1 A.U. in phospholipid magnesome containing EGF-IRDye 800CW as compared to 10.0 and 6.7 A.U. in WS and Lipo, respectively (FIG. 6).

Example 4

Analgesic Effect of Oxytocin Nasally Delivered in Phospholipid Magnesome as Compared to Two Control Carriers The analgesic effect of intranasal administration of Oxytocin in phospholipid magnesome composition was evaluated in female C57B1/6J mice. The acetic acid-induced pain mice model was used.

In this model, animals received analgesic treatment, then after predetermined time periods, pain was induced by 0.6% (v/v) acetic acid solution injected intraperitoneally at a dose of 10 ml/kg. The number of writhes in a 10 min period was counted, starting 5 min after the acetic acid injection. A writhe is characterized by a wave of contraction of the abdominal musculature followed by extension of at least one hind limb. Antinociception is expressed as percent inhibition of the number of writhes observed in treated animals in comparison to animals in the untreated group.

The Maximum Possible Effect (MPE) of different treatments is expressed as the inhibition percent of the number of writhes in a drug-treated animal group, when compared to the mean number of writhes measured in a group of untreated control mice according to the following equation.

MPE %=[Mean of writhes in untreated control group−Mean of writhes in treated group]/[Mean of writhes in untreated control group]*100

Twenty mice were divided into three equal treatment groups for testing three time points: 5, 30 or 120 min (n=5/group) and Untreated control group. The following formulations were prepared.

| | Phospholipid magnesome (% w/w) | Water solution % w/w | Liposome % w/w |
|---|---|---|---|
| oxytocin | 0.08 | 0.08 | 0.08 |
| PL | 3 | — | 3 |
| PG | 15 | — | — |
| Sodium alginate | 0.6 | — | 0.6 |
| Magnesium sulfate | 0.03 | — | — |
| DDW | To 100 | To 100 | To 100 |

Preparation: PL was dissolved in PG, Oxytocin was added and then 20% of the total DDW amount was added, through mixing. In a separate vessel, Sodium Alginate was dispersed in 10% of the total amount of DDW and mixed with Magnesium Sulfate aqueous solution (10 mg/ml). The PL solution was then added to the alginate gel through mixing, then the remaining DDW was added.

Oxytocin was administered nasally to mice from the three formulations at a dose of 0.4 mg/kg animal (~0.008 mg\10 µl/mouse).

FIG. 7 and the table below give the writhes counts and MPE % values, respectively, following treatment of mice with 0.4 mg/kg Oxytocin incorporated in various carriers. As shown in the bar diagram of FIG. 7, a significant decrease in writhes number was observed following treatment with Oxytocin from phospholipid magnesome (the darkest bar). The effect of the peptide incorporated in various controls (WS and Lipo) was lower by 2 folds, underscoring the enhanced delivery of Oxytocin from phospholipid magnesome.

Below are tabulated calculated MPE % values following Oxytocin administration to mice at a dose of 0.4 mg/kg from phospholipid magnesome and control nasal systems administrated at various time points before pain induction.

| Time (min) | Phospholipid magnesome | Water solution MPE % | Liposome |
|---|---|---|---|
| 5 | 63.5 | 35.8 | 30.8 |
| 30 | 63.9 | 27.8 | 25.8 |
| 120 | 58.0 | 29.8 | 19.2 |

Example 5

Local Safety

The effect of phospholipid magnesome on the nasal cavity was evaluated in rats. Female SD/H rats were divided into four groups:

Group 1—(phospholipid magnesome): Intranasal administration of phospholipid magensome composition as described in Example 1, Part II (15 µl/rat)

Group 2—(NS): Intranasal Normal saline (15 µl/rat).

Group 3—(SLS): Intranasal Sodium lauryl sulfate Solution (1% w/w), (15 µl/rat).

Group 4—Untreated control animals.

The animals received the treatments twice a day for one week. At the end of the experiment, animals were sacrificed, nasal cavities were removed and fixed in 3.7% Formaldehyde PBS. Sections of the nasal cavity were cut serially at 7 µm thickness and stained with Hematoxylin & Eosin. The sections were examined by professional histopathologist (Authority for Animal Facilities, Hebrew University of Jerusalem, Israel) by Olympus light microscope BX43 and Olympus digital camera DP21 with Olympus cellSens Entry 1.13 software (Olympus, Japan) using magnification ×10. Local toxicity was assessed by evaluating the histopathological alterations in different regions of the nasal cavity (cartilage and turbinate bone, lamina propria and submucosa, mucosal epithelium and lumen).

No pathological findings were observed in the histopathological analysis of the nasal cavities excised from rats treated with phospholipid magnesome or NS. The micrographs for these groups were similar to untreated control group showing intact mucosal epithelium, empty lumen and no infiltration of inflammatory cells. Overall, there was no evidence of inflammation. Turbinate bone integrity was preserved. Epithelium was normal with no evidence of erosion or ulceration and ciliated epithelium was intact. On the other hand, minimal proteinaceous material in the lumen and focal aggregations of neutrophils were observed in the positive control group treated with SLS. Micrographs corresponding to the four groups are presented in FIG. 8.

Example 6

Tramadol HCl-Containing Phospholipid Magnesome

| Ingredients | % w/w |
|---|---|
| Tramadol HCl | 10 |
| PL | 3 |
| PG | 15 |
| Sodium Alginate | 0.6 |
| Magnesium Sulfate | 0.01 |
| DDW | To 100 |

Preparation: PL was dissolved in PG, Tramadol and 20% of the total DDW amount were added, through mixing. In a separate vessel, Sodium Alginate was dispersed in 10% of the total amount of DDW and mixed with Magnesium Sulfate aqueous solution (10 mg/ml). The PL solution was then added to the alginate gel through mixing with an overhead stirrer (Heidolph digital 200 RZR-2000, Germany), then the remaining DDW was added.

Example 7

Rizatriptan Benzoate-Containing Phospholipid Magnesome

| Ingredients | % w/w |
|---|---|
| Rizatriptan Benzoate | 10 |
| PL | 3 |
| PG | 15 |
| Magnesium Sulfate | 0.03 |
| DDW | To 100 |

Preparation: PL was dissolved in PG, then Rizatriptan was added, through mixing. To this mixture, Magnesium Sulfate aqueous solution (10 mg/ml) was added through mixing with a magnetic stirrer, then the remaining DDW was added.

Example 8

Mannitol-Containing Phospholipid Magnesome

| Ingredients | % w/w |
|---|---|
| Mannitol | 10 |
| PL | 3 |
| PG | 15 |
| Magnesium Sulfate | 0.07 |
| DDW | To 100 |

Preparation: PL was dissolved in PG, then Mannitol was dispersed in the PL solution. To this mixture Magnesium Sulfate aqueous solution (10 mg/ml) was added through mixing with an overhead stirrer (Heidolph digital 200 RZR-2000, Germany), then DDW was added.

Example 9

Cannabidiol-Containing Phospholipid Magnesome

| Ingredients | % w/w |
|---|---|
| CBD | 1 |
| PL | 3 |
| PG | 25 |
| Ethanol Absolute (ETOH) | 15 |
| Magnesium Sulfate | 0.01 |
| DDW | To 100 |

Preparation: PL was dissolved in ETCH and PG mixture, then CBD was dissolved in the PL solution. To this solution, Magnesium Sulfate aqueous solution (10 mg/ml) was added through mixing with a magnetic stirrer then DDW was added.

Example 10

Cannabidiol-Containing Phospholipid Magnesome

| Ingredients | % w/w |
|---|---|
| CBD | 0.5 |
| PL | 5 |
| PG | 25 |
| ETOH | 17 |
| Magnesium Sulfate | 0.01 |
| DDW | To 100 |

The composition is prepared with a high shear mixer. PL was dissolved in ETOH and PG mixture, then CBD was dissolved in the PL solution. To this solution, Magnesium Sulfate aqueous solution (10 mg/ml) was added through mixing with a magnetic stirrer then DDW was added.

Example 11

Brotizolam-Containing Phospholipid Magnesome

| Ingredients | % w/w |
|---|---|
| Brotizolam | 0.1 |
| PL | 3 |
| PG | 15 |
| Carbopol 980 | 0.05 |
| Ammonium hydroxide | 0.05 |
| Magnesium Sulfate | 0.02 |
| DDW | To 100 |

PL was dissolved in PG. Brotizolam was added to the solution. In a separate vessel, Carbopol 980 was suspended in DDW and ammonium hydroxide was added. Then Magnesium Sulfate aqueous solution (10 mg/ml) was added to this mixture followed by adding the PL solution through mixing with an overhead stirrer (Heidolph digital 200 RZR-2000, Germany).

Example 12

Cannabidiol-Containing Phospholipid Magnesome

| Ingredients | % w/w |
|---|---|
| CBD | 1 |
| PL | 10 |
| PG | 40 |
| Vit E | 0.4 |
| Magnesium Sulfate | 0.03 |
| DDW | To 100 |

PL was dissolved in PG, then CBD and Vit E were dissolved in the PL solution. To this solution, Magnesium Sulfate aqueous solution (10 mg/ml) was added through mixing with a magnetic stirrer then DDW was added.

Example 13

Butorphanol Tartrate (BUT)-Containing Phospholipid Magnesome

| Ingredients | % w/w |
|---|---|
| BUT | 0.1 |
| PL | 2 |
| PG | 30 |
| Sodium Hydroxide | 0.5 |
| Magnesium Sulfate | 0.025 |
| DDW | To 100 |

Preparation: PL was dissolved in PG, then BUT was dissolved in the PL solution. To this solution, DDW and magnesium sulfate solutions were added through mixing with an overhead stirrer (Heidolph digital 200 RZR-2000, Germany). Finally, Sodium Hydroxide was added (for pH adjustment). Final pH—5.5.

Example 14

Ketoprofen (KET)-Containing Phospholipid Magnesome

| Ingredients | % w/w |
|---|---|
| KET | 20 |
| PL | 2 |
| Magnesium Sulfate | 0.025 |
| PG | 30 |
| Sodium Hydroxide (10%) | 40 |
| Hydrochloric Acid (32%) | 5.8 |
| DDW | To 100 |

Preparation: PL was dissolved in PG. In a separate vessel, KET was suspended in 20% of DDW, then Sodium Hydroxide Solution was added (to dissolve KET) and followed by the addition of Hydrochloric Acid (for pH adjustment) and the rest amount of DDW and magnesium sulfate solution wee added. Finally, the PL solution was added to this solution and mixed with an overhead stirrer (Heidolph digital 200 RZR-2000, Germany).

Example 15

Ketoprofen (KET)-Containing Phospholipid Magnesome

| Ingredients | % w/w |
|---|---|
| KET | 3 |
| PL | 2 |
| PG | 30 |
| Sodium Hydroxide (10%) | 10 |
| Magnesium sulfate | 0.02 |
| HCl solution (32%) | 2 |
| DDW | To 100 |

Preparation: PL was dissolved in PG. In a separate vessel, KET was suspended in 20% of DDW, then Sodium Hydroxide Solution was added (to dissolve KET) and followed by the addition of Hydrochloric Acid (for pH adjustment). The Magnesium solution, and the rest amount of DDW were added. Finally, the PL solution was added to this solution and mixed with an overhead stirrer (Heidolph digital 200 RZR-2000, Germany). Final pH—5.7

Example 16

Assessment of Phospholipid Magnesome Softness (More Fluid Bilayers Relative to Liposome) by Transition Temperature (Tm) Measurement by Differential Scanning Calorimetry (DSC)

Tm of the phospholipid was measured in the following compositions:

| Ingredients | phospholipid magnesome % w/w | Liposome % w/w |
|---|---|---|
| Magnesium sulfate | 0.03 | — |
| PL | 5 | 5 |
| PG | 15 | — |
| DDW | To 100 | To 100 |

The measurements were carried out using a Mettler Toledo DSC-1 STAR system (Toledo, China). Samples of 20 mg were placed in aluminum metal dishes. Tomograms were generated recording Tm values at a heating rate of 10° C./min within the temperature range of −50° C. to +50° C.

Results indicate that phospholipid magnesome systems had a Tm value of −7° C. vs. +7° C. for liposome. This lower Tm by 14° C. could be the result of a fluidization of the PL lamellae in phospholipid magnesome vesicles n comparison with classic liposome. The thermograms are shown in FIGS. 9A and 9B.

Example 17

Assessment of Drug Concentration in Plasma and Pharmacokinetic Parameters

Plasma concentration of Ketoprofen was measured following in vivo nasal administration and compared to oral administration. The experiment was carried out using Male Sprague Dawley (SD/Hsd) rats (Harlan, Israel).

The method of Ketoprofen extraction from plasma was validated according to FDA regulations for bio-analytical method validation, assessing precision, recovery, selectivity and linearity. The precision was 8.7%, the recovery was 96.6±5.5%, the limit of detection (LOD) was 0.84 mcg/ml, and the limit of quantification (LOQ) was 2.53 mcg/ml, Linear regression analysis of the plasma standard curve showed correlation with $R^2=1.00$ over the concentration range of 0.05-100 mcg/ml Ketoprofen. The calibration curve equation: Y=143453X, (Y=Area, X=Concentration).

Ketoprofen (14 mg/kg) was administered nasally from Ketoprofen new nanovesicular carrier (KET-phospholipid Magnesome) and compared to oral administration (KET-PO). The compositions are tabulated below.

| Compositions | | |
|---|---|---|
| Ingredients | KET -phospholipid magnesome % w/w | KET-PO % w/w |
| Ketoprofen (KET) | 20 | 2 |
| PL | 5 | — |
| PG | 30 | — |
| Sodium Hydroxide (10%) | 40 | 40 |
| Hydrochloric Acid (32%) | 5.8 | 5.8 |
| Magnesium sulfate | 0.02 | — |
| Methyl Cellulose | — | 2 |
| DDW | To 100 | To 100 |

Preparation: PL is dissolved in PG. In a separate vessel, KET is suspended in a part of water, then Sodium Hydroxide Solution is added (to dissolve KET) and followed by the addition of hydrochloric acid (for pH adjustment). The magnesium solution and the rest amount of DDW are added. Finally, the PL solution is added to this aqueous solution and mixed with an overhead stirrer (Heidolph digital 200 RZR-2000, Germany) or Polytron homogenizer. Final pH—5.4

Blood samples were collected from rats' tails at 10, 30, 60, 120, 180, 240 and 300 min post drug administration. The blood samples were centrifuged at 3k rpm for 10 min at 25° C. (HERMLE Z 160 M), and then 150 mcl of the plasma was taken. Plasma samples were frozen and kept at −20° C. until analysis.

A volume of 300 mcl of ACN was added to the plasma and mixed by vortex for 3 minutes at level 10, followed by the addition of 300 mcl of acetate buffer 0.05M with pH 5, and mixed by vortex for additional 1 minute at level 10. Then, the samples were centrifuged for 5 min at 14k rpm at 25° C. (HERMLE Z 160 M), and the supernatants were filtered through Bulk GHP Acrodisc® 13 mm syringe filter with 0.45 μm GHP membrane (Pall Corporation, USA), and transferred into pre-labeled auto injector vials before being injected into HPLC-UV.

The relative bioavailability (F %) was calculated according to the following equation:

The $AUC_{NVC}$ and $AUC_{PO}$ represent the means of individual AUC from nasal and oral experimental groups, respectively.

The pharmacokinetic study aimed to evaluate the influence of the new nanovesicular carrier on the absorption parameters of the drug model, Ketoprofen. For this purpose, Ketoprofen concentration was assessed in plasma of rats following drug administration from new nanovesicular carrier as compared to oral administration. Ketoprofen plasma concentration curves versus time are plotted in FIG. 10 (rectangular: nasal administration according to the invention; triangle oral administration).

Ketoprofen was assayed in rat plasma starting from 10 min post nasal or oral administration. Results are tabulated below.

| PK parameters | Nasal composition | Oral administration |
|---|---|---|
| $T_{1/2}$, min | 138.2 ± 21.1 | 328.7 ± 83.1 |
| Tmax, min | 10.0 ± 0.0 | 94.0 ± 12.4 |
| Cmax, mcg/ml | 43.7 ± 8.3 | 13.7 ± 5.9 |
| $AUC_{0-5\,hr}$ | 4130.4 ± 730.6 | 2642.1 ± 1153.3 |
| $T_{last}$, min | 300.00 ± 0.00 | 300 ± 0.00 |
| Bioavailability (relative to oral, %) | | 156.3 |

Results presented above show that very significant higher plasma concentrations (P<0.01) were detected 10 and 30 min after Ketoprofen administration in nasal vesicular nano-carrier. $C_{max}$ plasma values calculated for new nanovesicular carrier and oral administration were 43.65±8.30 and 13.68±5.91 mcg/ml, respectively. The $T_{max}$ values were 10 and 94 min for nasal vesicular carrier administration and oral administration, respectively.

These results above indicate that Ketoprofen was rapidly delivered from the nasal cavity to the systemic circulation following nasal administration showing that the phospholipid magnesome possesses enhanced delivery properties and enhanced effect for the first 90 minutes relative to the oral administration, with a very rapid onset of action and behaves similar to the oral administration for the next five tested hours.

Example 18

Cannabidiol-Containing Phospholipid Magnesome

| Ingredients | % w/w |
|---|---|
| CBD | 5 |
| PL | 5 |
| PG | 30 |
| Ethanol | 15 |
| Hemp Seed Oil (HSO) | 4 |
| Magnesium Sulfate | 0.03 |
| DDW | To 100 |

PL is dissolved in PG and Ethanol mixture, and then HSO is added. CBD is dissolved in this solution. Then, Magnesium Sulfate aqueous solution (10 mg/ml) is slowly added through vigorous mixing with a homogenizer. Finally, DDW is slowly added with mixing.

Example 19

Cannabidiol-Containing Phospholipid Magnesome

| Ingredients | % w/w |
|---|---|
| THC | 0.5 |
| PL | 5 |
| Vit E | 0.5 |
| PG | 30 |
| Olive Oil | 3 |
| Magnesium Sulfate | 0.03 |
| DDW | To 100 |

PL is dissolved in PG, then Vit E, Oil and THC are added to the PL solution. To this solution, Magnesium Sulfate aqueous solution (10 mg/ml) is added slowly through mixing with an overhead stirrer (Heidolph digital 200 RSR-2000, Germany).

Examples 20-21

Insulin-Containing Phospholipid Magnesome

|  | Example 20 ingredients % w/w | Example 21 ingredients % w/w |
|---|---|---|
| Insulin | 0.1 | 0.1 |
| PL | 3.0 | 3.0 |
| PG | 15.0 | 15.0 |
| Vitamin E | 0.3 | 0.3 |
| Magnesium sulfate | 1.0 | 5.0 |
| DDW | 80.6 | 76.6 |

Preparation: PL was dissolved in PG, then Vitamin E was added. In a separate vessel, Magnesium Sulfate was dissolved in DDW. The Magnesium solution was added gradually to the PL solution and mixed well. Finally, Insulin (from Bovine Pancreas-Sigma Aldrich, USA) was added and mixed well. The mixing through the entire preparation process was performed using an overhead Heidolph® stirrer (Heidolph Digital 200 RZR-2000, Germany).

Examples 22-23

Bacitracin-Containing Phospholipid Magnesome

|  | Example 22 ingredients % w/w | Example 23 ingredients % w/w |
|---|---|---|
| Bacitracin | 0.1 | 0.1 |
| PL | 3.0 | 3.0 |
| PG | 15.0 | 15.0 |
| Vitamin E | 0.3 | 0.3 |
| Magnesium sulfate | 10 | 20 |
| DDW | 71.6 | 61.6 |

PL was dissolved in PG, then Vitamin E was added. In a separate vessel, Magnesium Sulfate was dissolved in DDW. The Magnesium solution was added gradually to the PL solution and mixed well. Finally, Bacitracin (Sigma Aldrich, USA) was added and mixed well. The mixing through the entire preparation process was performed using an overhead Heidolph® stirrer (Heidolph Digital 200 RZR-2000, Germany).

Example 24

Tramadol HCl-Containing Phospholipid Magnesome

|  | ingredients % w/w |
|---|---|
| Tramadol HCl | 1.0 |
| PL | 3.0 |
| PG | 15.0 |
| Vitamin E | 0.3 |
| Magnesium sulfate | 5.0 |
| DDW | 75.7 |

PL was dissolved in PG, then Vitamin E was added. In a separate vessel, Tramadol HCl (Chemagis, Israel) was dissolved in DDW and followed by dissolving the Magnesium Sulfate. The aqueous solution of Tramadol HCl and Magnesium was added gradually to the PL solution and mixed well. The mixing through the entire preparation process was performed using an overhead Heidolph® stirrer (Heldoiph Digital 200 RZR-2000, Germany).

Example 25

Safinamide Mesylate-Containing Phospholipid Magnesome

|  | ingredients % w/w |
|---|---|
| Safinamide mesylate | 2.0 |
| PL | 5.0 |
| PG | 15.0 |
| Vitamin E | 0.5 |
| Magnesium sulfate | 0.5 |
| DDW | to 100 |

PL is dissolved in PG, then Vitamin E is added. In a separate vessel, Safinamide mesylate is dissolved in DDW and is added gradually to the PL solution and mixed well using an overhead Heidolph® stirrer (Heidolph Digital 200 RZR-2000, Germany). Finally, the Magnesium Sulfate is added to the composition and mixed.

Examples 26-34

Phospholipid Magnesome with Varying Mg Content

| ingredients | Ex. 26 % w/w | Ex. 27 %w/w | Ex. 28 % w/w | Ex. 29 % w/w | Ex. 30 % w/w | Ex. 31 % w/w | Ex, 32 % w/w | Ex. 33 % w/w | Ex. 34 % w/w |
|---|---|---|---|---|---|---|---|---|---|
| PL | 3.0 | 3.0 | 3.0 | 3.0 | 3.0 | 3.0 | 3.0 | 3.0 | 3.0 |
| PG | 15.0 | 15.0 | 15.0 | 15.0 | 15.0 | 15.0 | 15.0 | 15.0 | 15.0 |
| Vitamin E | 0.3 | 0.3 | 0.3 | 0.3 | 0.3 | 0.3 | 0.2 | 0.3 | 0.3 |
| Magnesium sulfate | 0.01 | 0.1 | 0.3 | 0.5 | 1.0 | 2.0 | 5.0 | 10.0 | 20.0 |
| DDW | 81.69 | 81.6 | 81.4 | 81.2 | 80.7 | 79.7 | 76.7 | 71.7 | 61.7 |

PL was dissolved in PG, then Vitamin E was added. In a separate vessel, Magnesium Sulfate was dissolved in DDW. The Magnesium solution was added gradually to the PL solution and mixed well using an overhead Heidolph® stirrer (Heidolph Digital 200 RZR-2000, Germany).

Example 35

Pramipexole-Containing Phospholipid Magnesome

| ingredients % w/w |
|---|
| Pramipexole | 1.00 |
| Propylene glycol (PG) | 20.0 |
| Phospholipon 90 G (PL) | 3.00 |
| α-D- tocopheryl acetate (Vit E) | 0.50 |
| Magnesium sulfate anhydrous (MgSO$_4$) | 0.10 |
| Sodium hydroxide (NaOH) | 0.05 |
| Double distilled water (DDW) | To 10 0 |

PL was mixed with PG using an overhead stirrer at 700 rpm (Heidolph, Hei Torque 200) until completely dissolved. Vit E was added and mixed well. MgSO$_4$ was dissolved in about one third of the water amount, and the solution was added to the above PG solution through mixing.

In a separate vessel, NaOH 1% w/v solution was added to two thirds of the water amount. Pramipexole was dissolved in the above water solution. pH was measured and, if needed, adjusted to ~4.5 with NaOH. This Pramipexole solution was then added through mixing at 700 rpm to the above system. The mixing was further continued for 5 min.

Example 36

Pramipexole-Containing Phospholipid Magnesome

| ingredients % w/w |
|---|
| Pramipexole | 0.50 |
| Propylene glycol (PG) | 20.0 |
| Phospholipon 90 G (PL) | 3.00 |
| α-D-tocopheryl acetate (Vit E) | 0.50 |
| Magnesium sulfate anhydrous (MgSO$_4$) | 0.10 |
| Sodium hydroxide (NaOH) | 0.023 |
| Double distilled water (DDW) | To 100 |

PL was mixed with PG using an overhead stirrer at 700 rpm (Heidolph, Hei Torque 200) until completely dissolved. Vit E was added and mixed well. MgSO$_4$ was dissolved in about one third of the water amount, and the solution was added to the above PG solution through mixing.

In a separate vessel, NaOH 1% w/v solution was added to two thirds of the water amount. Pramipexole was dissolved in the above water solution. pH was measured and, if needed, adjusted to ~4.5 with NaOH. This Pramipexole solution was then added through mixing at 700 rpm to the above system. The mixing was further continued for 5 min.

Example 37

Effect of Nasal Administration of Pramipexole Phospholipid Magnesome Versus Drug Oral Administration in Mice Model for Parkinson Disease with Locomotor Impairment The goal of the experiment reported below was to evaluate the effect of nasal administration of Pramipexole Phospholipid Magnesome on impaired locomotor activity in model mice for Parkinson's disease in comparison with oral administration of the drug and untreated animals. The animal model was obtained by administering Reserpine to mice.

Experimental Protocol

Compositions

The compositions tested were the one illustrated in Example 36 (0.5% w/w Pramipexole in Phospholipid Magnesome) and an aqueous solution of 0.5% w/w Pramipexole in water for oral administration, prepared by adding NaOH 1% w/v solution to DDW to achieve NaOH at concentration of 0.022% w/w, followed by dissolution of the drag in the alkaline solution.

Animals

All procedures carried out on animals were according to The National Institutes of Health regulations and were approved by the Committee for Animal Care and Experimental Use of the Hebrew University of Jerusalem.

The experiment was performed on fifteen male CD-1 ICR mice (27-32 g). Mice were housed under standard conditions of light and temperature in plastic cages in the specific-pathogen unit (SPF) of the pharmacy school at the Hebrew University of Jerusalem. Animals were kept in separated cages with smooth flat floor and provided with unlimited access to water and food.

Treatments

The mice were divided randomly into two drug treated groups, Pramipexole Phospholipid Magnesome administrated nasally (n=6), Pramipexole oral solution (n=4) and one untreated control group (n=5). Animals in the treatment groups received Pramipexole nasally from Phospholipid Magnesome or orally from solution at a dose of 3 mg/kg. Twenty minutes after the treatments, the behavioral testing was assessed. To rule out the effect of anesthesia, animals in the untreated control groups were anesthetized at the same time points before the behavioral testing.

On the first and eighth days of the experiment, the animals in the three groups received intraperitoneal injections of Reserpine at doses of 4 and 3 mg/kg, respectively. Reserpine injection was prepared in DDW containing 0.1% DMSO and 0.3% Tween 80. The suspension was further processed for 20 min at 50% power ratio using an Ultrasonic processor, Sonic-650WT-V2 Ultrasonic processor. Sonic Series, MRC Ltd, Holon, Israel.

Behavioral Testing

The behavioral tests (open field test and ptosis score) were performed on day 9 of the experiment, 23 hours after last Reserpine injection and 20 min following nasal or oral Pramipexole administration.

Open Field Test

Spontaneous locomotor activity of animals was measured using the open field test. Mice were placed in the center of a cage (29×28.5×30 cm), with the floor divided into nine equal squares. The number of squares crossed was counted during 5 min with no habituation session.

Normal animal moves in the cage and crosses squares on the floor. Reserpinized animal suffers from akinesia (cannot move) and crosses much less squares. Efficient treatment will reverse animal's behavior to normal.

Ptosis Score

Ptosis is the eye closure due to drooping of the upper eyelid. Reserpine induced ptosis was visually determined. Ptosis was recorded on a 0-4 scale, in which 0 represents eyes completely shut, and 4 completely open.

Normal animal has a ptosis score of 4. The score for reserpinized animals is reduced to 0-1. Efficient treatment will reverse the score to normal.

Results of the Open Field Test

The number of squares crossed (Mean±SD) in the open field test by Parkinson's mice model treated are tabulated below.

| Group | Nasal Pramipexole Phospholipid Magnesome | Pramipexole Oral | Untreated |
|---|---|---|---|
| Number of squares crossed | 81.8 ± 25.3 | 27.5 ± 30.1 | 2.6 ± 3.6 |

*Normal animals cross more than 100 squares.

The results are also presented graphically in the form of a bar diagram in FIG. 11.

The results pertaining to the open field test indicate that mice treated nasally with Pramipexole Phospholipid Magnesome expressed higher locomotor activity and crossed 81.8±25.3 squares. The animals in the Pramipexole orally treated and the untreated groups crossed only 27.5±30.1 and 2.6±3.6 squares, respectively (FIG. 11). The results show that the nasal administration of Pramipexole Phospholipid Magnesome significantly (p<0.01) enhanced the locomotor activity by 300% in comparison with oral treatment.

Results of Ptosis Score

Ptosis scores for Parkinson's mice model treated (Mean±SD) are tabulated below.

| Group | Nasal Pramipexole Phospholipid Magnesome | Pramipexole oral | Untreated |
|---|---|---|---|
| Ptosis score | 3.3 ± 0.7 | 2.0 ± 1.4 | 1.2 ± 0.4 |

*Normal animal has a ptosis score of 4.

The results are also presented graphically in the form of a bar diagram in FIG. 12.

In the evaluation of Reserpine-induced ptosis, a score of 3.3±0.7 was recorded for nasal. Pramipexole Phospholipid Magnesome as compared to only 2.0±1.4 and 1.2±0.4 for the orally treated and the untreated groups, respectively (FIG. 12).

These results indicate enhanced anti-Parkinson's effect of Pramipexole achieved by means of nasal administration using Phospholipid Magnesome in comparison with oral administration.

Example 38

Effect of Nasal Administration of Pramipexole Phospholipid Magnesome Versus Drug Oral Administration in Mice Model for Parkinson Disease with Locomotor Impairment The goal of the experiment was to evaluate the effect of nasal administration of Pramipexole Phospholipid Magnesome on impaired locomotor activity in model mice for Parkinson's disease in comparison with oral administration of the drug and untreated animals. The animal model was obtained by administrating Reserpine to mice.

Experimental Protocol

Compositions

The compositions tested were the one illustrated in Example 36 (0.5% w/w Pramipexole in Phospholipid Magnesome) and an aqueous solution of 0.5% w/w Pramipexole in water for oral administration, prepared by adding NaOH 1% w/v solution to DDW to achieve NaOH at concentration of 0.022% w/w, followed by dissolution of the drag in the alkaline solution.

Animals

All procedures carried out on animals were according to The National Institutes of Health regulations and were approved by the Committee for Animal Care and Experimental Use of the Hebrew University of Jerusalem.

This experiment was performed on 21 male CD-1 ICR mice (25-29 g). Mice were housed under standard conditions of light and temperature in plastic cages in the specific-pathogen unit (SPF) of the pharmacy school at the Hebrew University of Jerusalem. Animals were kept in separated cages with smooth flat floor and provided with unlimited access to water and food.

Treatments

The mice were divided randomly into two drug treated groups (Pramipexole Phospholipid Magnesome administrated nasally, and pramipexole oral solution) and one untreated control group (n=7/group). Animals in the treatment groups received Pramipexole at a dose of 3 mg/kg nasally from Phospholipid Magnesome or Pramipexole orally from solution, 20 min before the behavioral testing. To rule out the effect of anesthesia, animals in the untreated control groups were anesthetized at the same time points before the behavioral testing.

On the first and sixth days of the experiment, the animals of the three groups received an intraperitoneal injections of Reserpine at a dose of 3 mg/kg.

Behavioral Testing

The behavioral tests (open filed test, ptosis score and bar catalepsy test) were performed on day 7 of the experiment, 23 hours after last Reserpine injection. Open field test and ptosis score were assessed 20 min following nasal or oral Pramipexole administration. Bar catalepsy test was carried out immediately after the open field test (25 min following Pramipexole administration).

Open Field Test

The same protocol as in Example 37.

Ptosis Score

The same protocol as in Example 37.

Bar Catalepsy Test

Cataleptic immobility is regarded as an animal equivalent of akinesia and is demonstrated by an animal allowing its body to be placed in and maintain abnormal or unusual postures. We used the bar test to determine the ability of nasal administration of Pramipexole in Phospholipid Magnesome to reduce the duration of catalepsy in Parkinson's mice model in comparison with oral administration of the drug.

Twenty-five minutes after nasal and oral treatments, both fore paws of the mice were placed on a horizontal bar (diameter, 0.7 cm) 5 cm above the surface and then gently released. The catalepsy duration retained in this unusual position was recorded in seconds from the moment when an animal was released to the moment when it shifted its front paws from the initial position on the bar. The trial ended either when the animal started to move or after 60 s of immobility (cut off time).

Normal animal releases the bar immediately. Reserpinized animal suffers from catalepsy cannot return to normal position and therefore stays on the bar for longer time. Efficient treatment will reverse animal's behavior to normal.
Results of the Open Field Test The number of squares crossed (Mean±SD) in the open field test by Parkinson's mice model treated are tabulated below.

| Group | Nasal Pramipexole Phospholipid Magnesome | Pramipexole oral | Untreated |
|---|---|---|---|
| Number of squares crossed. | 109.0 ± 29.8 | 37.4 ± 22.5 | 28.5 ± 32.4 |

*Normal animals cross more than 100 squares.

The results are also presented graphically in the form of a bar diagram in FIG. 13.

The results pertaining to the open field test indicate that mice treated nasally with Pramipexole Phospholipid Magnesome expressed higher locomotor activity and crossed 109.0±29.8 squares. The animals in the Pramipexole orally treated and the untreated groups crossed only 37.4±22.5 and 28.5±32.4 squares, respectively (FIG. 13). The results are significant: $p<0.01$ for Pramipexole Phospholipid Magnesome versus Pramipexole oral and $p<0.001$ for Pramipexole Phospholipid Magnesome versus untreated control.

Results of the Bar Catalepsy Test

Catalepsy duration by the bar test (Mean±SD) for Parkinson's mice model treated are tabulated below.

| Group | Nasal Pramipexole Phospholipid Magnesome | Pramipexole oral | Untreated |
|---|---|---|---|
| Catalepsy duration (sec) | 0.8 ± 0.6 | 9.0 ± 8.3 | 21.3 ± 18.7 |

*catalepsy duration measured by bar test for normal animals is 0 sec.

The results are also presented graphically in the form of bar diagram in FIG. 14.

The results pertaining to the bar catalepsy test indicate that nasal administration of Pramipexole from Phospholipid Magnesome reduced the catalepsy duration after 25 min from 21.3±18.7 in the reserpinized untreated animals to 0.8±0.6 sec ($p<0.001$). Oral administration of the same dose led to mild and non-significant reduction in the catalepsy duration (9.0±8.3 sec).

Results of Ptosis Score

Ptosis scores for Parkinson's mice model treated (Mean±SD) are tabulated below.

| Group | Nasal Pramipexole Phospholipid Magnesome | Pramipexole oral | Untreated |
|---|---|---|---|
| Ptosis score | 3.7 ± 0.5 | 1.7 ± 1.1 | 1.4 ± 1.0 |

*Normal animal has a ptosis score of 4.

The results are also presented graphically in the form of a bar diagram in FIG. 15.

In the evaluation of Reserpine induced ptosis, a score of 3.7±0.5 was recorded for Pramipexole Phospholipid Magnesome as compared to only 1.7±1.1 and 1.4±1.0 for the orally treated and the untreated groups, respectively (FIG. 15). The results of these experiments confirm the finding illustrated in Example 37 and show that the nasal administration of Pramipexole Phospholipid Magnesome significantly increased the locomotor activity by 300% in comparison with oral treatment. Furthermore, the nasal treatment completely reversed the reserpine induced catalepsy. These finding point towards the ability of nasal administration of Pramipexole Phospholipid magnesome to improve the treatment of Reserpine induced Parkinson's in mice.

The invention claimed is:

1. A nasally administrable composition comprising at least one active substance carried by a magnesium-containing vesicular carrier, said carrier comprising glycol, phospholipids, water, and at least one magnesium source, wherein the composition comprises from 5 to 50% by weight propylene glycol, from 0.2 to 10% by weight phospholipids, not less than 20% by weight water and from 0.01 to 1.0% by weight magnesium salt.

2. The composition of claim 1, further comprising an antioxidant, a mucoadhesive agent or both.

3. The composition according to claim 1, which is free of aliphatic monohydroxy alcohol.

4. The composition according to claim 2, wherein the magnesium salt is magnesium sulfate and the mucoadhesive agent is an alginate salt.

5. The composition according to claim 1, further comprising a vegetable oil.

6. The composition of claim 1, wherein the active substance is an analgesic, antimigraine and/or antipyretic agent.

7. The composition of claim 6, wherein the analgesic, antimigraine and antipyretic agent is selected from the group consisting of tramadol, ketoprofen, rizatriptan and pharmaceutically acceptable salts thereof.

8. The composition of claim 1, wherein the active substance is an opioid.

9. The composition of claim 8, wherein the opioid is butorphanol or a pharmaceutically acceptable salt thereof.

10. The composition of claim 1, wherein the active substance is an anti-Parkinson drug.

11. The composition of claim 10, wherein the anti-Parkinson drug is selected from the group consisting of safinamide, pramipexole and pharmaceutically acceptable salts thereof.

12. The composition of claim 1, wherein the active substance is a sedative and/or hypnotic drug.

13. The composition of claim 12, wherein the sedative and/or hypnotic drug is brotizolam or a pharmaceutically acceptable salt thereof.

14. The composition of claim 1, wherein the active substance is a peptide or a polypeptide.

15. The composition according to claim 14, comprising a peptide hormone selected from the group consisting of insulin, oxytocin, and bacitracin.

16. The composition according to claim 1, wherein the active substance is mannitol.

17. A method of administering an active substance to a mammal in need thereof, comprising intranasal administration of the composition according to claim 1.

18. A method according to claim 17, wherein the composition further comprises an antioxidant, a mucoadhesive agent or both.

19. A method according to claim 17, wherein the composition is free of aliphatic monohydroxy alcohol.

20. A method according to claim 17, wherein the active substance is selected from the group consisting of an analgesic, antimigraine and/or antipyretic agent; an opioid; an anti-Parkinson drug; and a sedative and/or hypnotic drug.

21. A method according to claim 17, wherein the active substance is selected from the group consisting of a peptide and a polypeptide.

* * * * *